(12) United States Patent
Kuriyama et al.

(10) Patent No.: US 8,524,953 B2
(45) Date of Patent: Sep. 3, 2013

(54) ALCOHOL PRODUCTION METHOD BY REDUCING ESTER OR LACTONE WITH HYDROGEN

(75) Inventors: Wataru Kuriyama, Hiratsuka (JP); Yasunori Ino, Hiratsuka (JP); Osamu Ogata, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 13/611,381

(22) Filed: Sep. 12, 2012

(65) Prior Publication Data

US 2013/0006020 A1    Jan. 3, 2013

Related U.S. Application Data

(62) Division of application No. 12/553,544, filed on Sep. 3, 2009, now Pat. No. 8,288,575.

(30) Foreign Application Priority Data

Sep. 9, 2008 (JP) ................................. 2008-230916
Jul. 16, 2009 (JP) ................................. 2009-167704

(51) Int. Cl.
   *C07C 29/147*   (2006.01)
   *C07F 5/02*     (2006.01)
   *B01J 31/14*    (2006.01)

(52) U.S. Cl.
   USPC ................................. 568/814; 556/8; 502/162

(58) Field of Classification Search
   USPC ............................. 556/8; 502/162; 568/814
   See application file for complete search history.

(56) References Cited

U.S. PATENT DOCUMENTS

| 6,720,439 B1 | 4/2004 | Ohkuma et al. |
| 8,288,575 B2 * | 10/2012 | Kuriyama et al. ............... 556/8 |

FOREIGN PATENT DOCUMENTS

| CN | 101137601 A | 3/2008 |
| CN | 101142155 A | 3/2008 |
| JP | 51-8203 A | 1/1976 |
| JP | 2003-104993 A | 4/2003 |
| WO | 2006/106483 A1 | 10/2006 |
| WO | 2006/106484 A1 | 10/2006 |
| WO | 2008/065588 A1 | 6/2008 |

OTHER PUBLICATIONS

The Late Homer Adkins, "Catalytic Hydrogenation of Esters to Alcohol," Organic Reactions, 1954, pp. 1-27.
Studer et al., "Catalytic Hydrogenation of Chiral a-Amino and a-Hydroxy Esters at Room Temperature with Nishimura Catalyst without Racemization," Adv. Synth. Catal., 2001, vol. 343, No. 8, pp. 802-808.
Grey et al., "Anionic Metal Hydride Catalysts. 2. Application to the Hydrogenation of Ketones, Aldehydes, Carboxylic Acid Esters, and Nitriles," J. Am. Chem. Soc. 1981, No. 103, pp. 7536-7542.
Teunissen et al. "Homogeneous ruthenium catalyzed hydrogenation of esters to alcohols," Chem. Commun., 1998, pp. 1367-1368.
Van Engelen et al., "Suitable ligands for homogeneous ruthenium-catalyzed hydrogenolysis of esters," J. of Mol. Catal. A:Chem., 2003, 185-192.
Zhang et al. "Efficient Homogeneous Catalytic Hydrogenation of Esters to Alcohols," Agnew. Chem. Int. Ed., 2006, No. 45, 1113-1115.
T. Li, "Hydrogenation of Benzonitrile to Benzylamine Catalyzed by Ruthenium Hydride Complexes with P-NH-NH-P. Tetradentate Ligands: Evidence for a Hydridic- Protonic Outer Sphere Mechanism," Organometallics, 2007, No. 26, 5940-5949.
Clarke et al., "Hydrogenation of Aldehydes, Esters, Imines, and Ketones Catalyzed by a Ruthenium Complex of a Chiral Tridenate Ligand," Organometallics, 2007, No. 26, pp. 16-19.
Saudan et al. "Dihydrogen Reduction of Carboxylic Esters to Alcohols under the Catalysis of Homogeneous Ruthenium Complexes: High Efficiency and Unprecedented Chemoselectivity," Agnew. Chem. Int. Ed., 2007, No. 46, 7473-7476.
Guo et al. "Enantioselective Tandem Micheal Addition/H2-Hydrogenation Catalyzed by Ruthenium Hydride Borohydride Complexes Containing B-aminophosphine Ligands," J. Am. Chem. Soc. 2005, No. 127, 516-517.
T. Li et al., "Dihydridoamine and Hydridoamido Complexes of Ruthenium (II) with a Tetradentate P-N-N-P. Donor Ligand," Organometallics, Am. Chem. Soc., 2004, No. 23, pp. 6239-6247.
Saudan et al., "Dihydrogen Reduction of Carboxylic Esters to Alcohols under the Catalysis of Homogeneous Ruthenium Complexes: High Efficiency and Unprecedented Chemoselectivity," Angewandt Chemie. Int. Ed., 46, 2007, pp. 7473-7476.
Zhang et al., "Efficient Homogeneous Catalytic Hydrogenation of Esters to Alcohols," Angewandt Chemie. Int. Ed., 45, 2006, pp. 1113-1115.
Chinese Patent Office, Chinese Office Action issued in corresponding CN Application No. 200910168724.6, dated May 27, 2013.
Chinese Patent Office, Chinese Search Report issued in corresponding CN Application No. 200910168724.6, dated May 27, 2013.

\* cited by examiner

*Primary Examiner* — Charanjit Aulakh
(74) *Attorney, Agent, or Firm* — Sughrue Mion, PLLC

(57) ABSTRACT

Provided is an alcohol production method comprising the step of reducing an ester or a lactone with hydrogen to produce a corresponding alcohol without addition of a base compound by using, as a catalyst, a ruthenium complex represented by the following general formula (1):

$$RuH(X)(L^1)(L^2)_n \qquad (1)$$

wherein
 X represents a monovalent anionic ligand,
 $L^1$ represents a tetradentate ligand having at least one coordinating phosphino group and at least one coordinating amino group or a bidentate aminophosphine ligand having one coordinating phosphino group and one coordinating amino group, and
 $L^2$ represents a bidentate aminophosphine ligand having one coordinating phosphino group and one coordinating amino group, provided that
 n is 0 when $L^1$ is the tetradentate ligand, and n is 1 when $L^1$ is the bidentate aminophosphine ligand.

5 Claims, No Drawings

ALCOHOL PRODUCTION METHOD BY REDUCING ESTER OR LACTONE WITH HYDROGEN

CROSS-REFERENCE TO RELATED APPLICATIONS

This application is a divisional of U.S. patent application Ser. No. 12/553,544 (now allowed) filed on Sep. 3, 2009 which claims priority from Japanese Patent Application No. 2008-230916 filed on Sep. 9, 2008 and Japanese Patent Application No. 2009-167704 filed on Jul. 16, 2009, the entire contents of which are incorporated herein by reference.

BACKGROUND OF THE INVENTION

1. Field of the Invention

The present invention relates to an alcohol production method by reducing an ester or a lactone with hydrogen.

2. Brief Description of the Related Art

Methods for obtaining alcohols by reducing esters and lactones are important in chemical synthesis. For obtaining such reactions, the following methods have been proposed: a method in which a stoichiometric amount or more of a metal hydride compound such as silyl hydride, sodium borohydride and lithium aluminium hydride is used; and a method in which catalytic hydrogenation reduction is conducted using molecular hydrogen. The former method has problems including: a great amount of waste generated from a reducing agent; and a safety concern raised by the use of a highly-reactive reducing agent. For this reason, recently, the latter method which is an environmentally friendly technology has been more actively developed and examined, regardless of heterogeneous and homogeneous reductions.

For example, Japanese Unexamined Patent Application Publication No. Sho 51-8203 and Org. React., 1954, 8, 1 propose examples of the heterogeneous hydrogenation reduction. However, such proposals have a problem that a high temperature condition or a high pressure condition, or both of the conditions are needed for the reduction, and other problems. Meanwhile, Adv. Synth. Cat., 2001, 343, 802 describes a production method under such a condition that racemization of an optically active ester may not be involved. However, the production method has a problem that, when the ester serving as the substrate has an aromatic ring, side-reactions frequently occur to produce, for example, alcohols with the aromatic ring reduced, thus exhibiting a low selectivity. Moreover, the production method has a disadvantage in terms of cost that a large amount of very expensive catalysts have to be used. Accordingly, the method is difficult to industrially put into practical use.

As for the homogeneous reduction, the utilization of a ruthenium complex including a phosphine ligand has been proposed in many documents.

For example, J. Am. Chem. Soc. 1981, 103, 7536, Chem. Commun. 1998, 1367, and J. Mol. Catal. A: Chem., 2003, 206, 185 disclose methods in which monophosphine, diphosphine, triphosphine and tetraphosphine ligands, and the like are used. Particularly when a tridentate triphosphine ligand is used, a relatively high hydrogenation activity is demonstrated. However, when an ester is not activated for a reduction, a fluorinated compound having a large environmental load has to be used as a solvent. This kind of problem makes the methods difficult to industrially put into practical use. Angew. Chem. Int. Ed. 2006, 45, 1113 and Organomet. 2007, 26, 16 disclose hydrogenation reduction of esters with a ruthenium complex including a tridentate diaminophosphine or aminodiphosphine ligand. In the method of Angew. Chem. Int. Ed. 2006, 45, 1113, carbon tetrachloride used when a ligand and a complex are prepared is environmentally harmful, and its production is banned in most of the world. Moreover, the reaction needs to be conducted at a low temperature. Accordingly, the method has a lot of industrial disadvantages. The method disclosed in Organomet. 2007, 26, 16 has difficulties that: a complex is prepared while being irradiated with microwaves; the hydrogenation of esters needs to be conducted at a high temperature of 140 to 150° C.; high yield is obtained only when esters are fluorinated because of the activation for a reduction; and so forth. WO2006/106483, WO2006/106484, WO2008/065588 and Angew. Chem. Int. Ed. 2007, 46, 7473 disclose efficient ester hydrogenation reduction methods using a ruthenium catalyst including bidentate and tetradentate aminophosphine and iminophosphine as ligands. In the methods, it is necessary to use an alkali metal alkoxide as a base when the reaction is conducted. Thus, the methods have a problem that the decomposition of the compound or racemization occurs in reducing a substrate having a base-labile functional group or reducing an ester having asymmetric carbon. Meanwhile, J. Am. Chem. Soc. 2005, 127, 516, Japanese Patent Application Publication No. 2003-104993 and other documents describe a ruthenium complex including an aminophosphine or a diphosphine and a diamine as ligands. Such a ruthenium complex is reported to reduce a carbonyl group without adding a base. However, the ruthenium complex reduces only a ketone, and has difficulty in reducing an ester group that is present together with the ketone. Meanwhile, complexes as used in the present invention have been prepared by a multi-stage method as disclosed in, for example, Organomet. 2004, 23, 6239 and Organomet. 2007, 26, 5940. Specifically, in the method: an iminophosphine ligand is reduced in advance; a complex is prepared from the ligand and a ruthenium precursor; thereafter the complex is further reduced.

SUMMARY OF THE INVENTION

Accordingly, an object of the present invention is to provide an alcohol production method from an ester or a lactone at high yield and at high catalytic efficiency under relatively moderate conditions while side reactions and the like are suppressed, by using a complex and a ligand which can be prepared relatively easily. Further, the method for producing an alcohol is industrially efficient since the complex is prepared relatively easily.

As a result of intensive studies conducted taking the above-described problems into consideration, the present inventors have discovered that it is possible to produce alcohols from esters or lactones at high yield and at high catalytic efficiency without adding a base compound while side-reactions and the like are suppressed, by using, as a catalyst, a ruthenium complex including a tetradentate ligand, which has at least one coordinating phosphino group and at least one coordinating amino group, or two bidentate aminophosphine ligands, which have one coordinating phosphino group and one coordinating amino group. Thus, the present invention has been achieved.

More specifically, the present invention relates to the following aspects [1] to [9].

[1] An alcohol production method including the step of reducing an ester or a lactone with hydrogen to produce a corresponding alcohol without addition of a base compound by using, as a catalyst, a ruthenium complex represented by the following general formula (1):

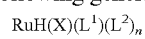

wherein X represents a monovalent anionic ligand, $L^1$ represents a tetradentate ligand having at least one coordinating phosphino group and at least one coordinating amino group or a bidentate aminophosphine ligand having one coordinating phosphino group and one coordinating amino group, and $L^2$ represents a bidentate aminophosphine ligand having one coordinating phosphino group and one coordinating amino group, provided that n is 0 when $L^1$ is the tetradentate ligand, and n is 1 when $L^1$ is the bidentate aminophosphine ligand.

[2] The production method described in [1], wherein X in the complex represented by the general formula (1) is $BH_4$.

[3] The production method described in [1] or [2], wherein the tetradentate ligand represented by $L^1$ in the complex represented by the general formula (1) further has one coordinating phosphorus atom and one coordinating nitrogen atom.

[4] The production method described in [3], wherein $L^1$ in the complex represented by the general formula (1) is a tetradentate ligand represented by the following general formula (2):

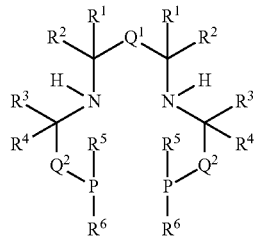

(2)

wherein $R^1$, $R^2$, $R^3$, $R^4$, $R^5$ and $R^6$, which may be same or different, each represent a hydrogen atom, an alkyl group which may have a substituent, an aralkyl group which may have a substituent, an aryl group which may have a substituent, or a cycloalkyl group which may have a substituent, $R^1$ and another $R^1$, $R^1$ and either $R^2$, $R^3$ or $R^4$, $R^3$ and $R^4$, or $R^5$ and $R^6$ may bond to each other to form a ring, and $Q^1$ and $Q^2$, which may be same or different, each represent a divalent arylene group which may have a substituent, an alkylene group which may have a substituent, or a bond.

[5] The production method described in [1] or [2], wherein $L^1$ and $L^2$ in the complex represented by the general formula (1), which may be same or different, each represent a bidentate aminophosphine ligand represented by the following general formula (3):

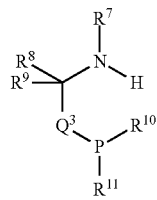

(3)

wherein $R^7$, $R^8$, $R^9$, $R^{10}$ and $R^{11}$, which may be same or different, each represent a hydrogen atom, an alkyl group which may have a substituent, an aryl group which may have a substituent, an aralkyl group which may have a substituent, or a cycloalkyl group which may have a substituent, $R^7$ and $R^8$ or $R^9$, $R^8$ and $R^9$, or $R^{10}$ and $R^{11}$ may bond to each other to form a ring, and $Q^3$ represents a divalent arylene group which may have a substituent, an alkylene group which may have a substituent, or a bond.

[6] The production method described in [4], wherein the complex is obtained by reducing a ruthenium complex including a tetradentate ligand represented by the following general formula (4) or (5):

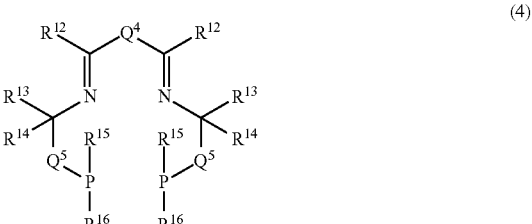

(4)

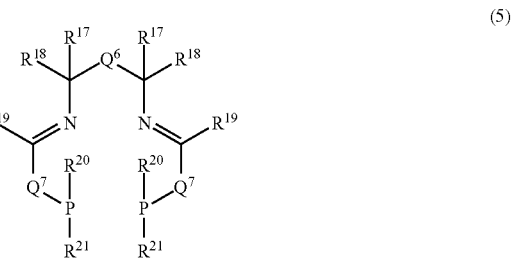

(5)

wherein $R^{12}$, $R^{13}$, $R^{14}$, $R^{15}$, $R^{16}$, $R^{17}$, $R^{18}$, $R^{19}$, $R^{20}$ and $R^{21}$, which may be same or different, each represent a hydrogen atom, an alkyl group which may have a substituent, an aryl group which may have a substituent, an aralkyl group which may have a substituent, or a cycloalkyl group which may have a substituent, $R^{12}$ and another $R^{12}$, $R^{12}$ and $R^{13}$ or $R^{14}$, $R^{13}$ and $R^{14}R^{15}$, and $R^{16}$, $R^{17}$ and another $R^{17}$, $R^{19}$ and $R^{17}$ or $R^{18}$, or $R^{20}$ and $R^{21}$ may bond to each other to form a ring, and $Q^4$, $Q^5$, $Q^6$ and $Q^7$, which may be same or different, each represent a divalent arylene group which may have a substituent, an alkylene group which may have a substituent, or a bond, the ruthenium complex being represented by a general formula (6):

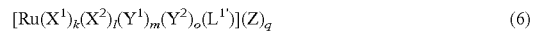

wherein $X^1$ and $X^2$ each independently represent a monovalent anionic ligand, $Y^1$ and $Y^2$ each independently represent a neutral monodentate ligand, Z represents a monovalent anion that does not coordinate to a metal, and $L^{1'}$ represents the tetradentate ligand represented by the general formula (4) or (5), provided that k, l, m and o are each a natural number between 0 to 2 inclusive, and satisfy $0 \leq k+l+m+o \leq 2$, and q is 0 when k+l=2, q is 1 when k+l=1, and q is 2 when k+l=0.

[7] The production method described in [5], wherein which the complex is obtained by reducing a ruthenium complex including a bidentate aminophosphine ligand represented by the following general formulae (7a) or (7b):

(7a)

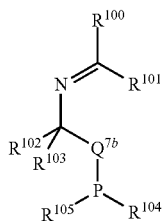

(7b)

wherein $R^{22}$, $R^{23}$, $R^{24}$, $R^{25}$, $R^{100}$, $R^{101}$, $R^{102}$, $R^{103}$, $R^{104}$, and $R^{105}$, which may be same or different, each represent a hydrogen atom, an alkyl group which may have a substituent, an aryl group which may have a substituent, an aralkyl group which may have a substituent, or a cycloalkyl group which may have a substituent, $R^{22}$ and $R^{23}$, $R^{24}$ and $R^{25}$, or $R^{104}$ and $R^{105}$ may bond to each other to form a ring, and $Q^{7a}$ and $Q^{7b}$ each represent a divalent arylene group which may have a substituent, an alkylene group which may have a substituent, or a bond, the ruthenium complex being represented by a general formula (6'):

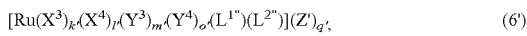  (6')

wherein $X^3$ and $X^4$ each independently represent a monovalent anionic ligand, $Y^3$ and $Y^4$ each independently represent a neutral monodentate ligand, Z' represents a monovalent anion that does not coordinate to a metal, and $L^{1''}$ and $L^{2''}$, which may be same or different, each represent the bidentate aminophosphine ligand represented by the general formula (7a) or (7b), provided that k', l', m' and o' are each a natural number between 0 to 2 inclusive, and satisfy $0 \leq k'+l'+m'+o' \leq 2$, and q' is 0 when k'+l'=2, q' is 1 when k'+l'=1, and q' is 2 when k'+l'=0.

[8] The production method described in any one of [1] to [7], wherein the prepared complex is used as the catalyst without being isolated from a complex preparing solution.

[9] The production method described in any one of [1] to [8], in which the ester or the lactone is an optically active substance, and the obtained alcohol holds an optical purity of 90% or more of that of the ester or lactone reduced with hydrogen.

The production method of the present invention enables alcohols to be produced from an ester and a lactone at high yield and at high catalytic efficiency under relatively low hydrogen pressure and reaction temperature which are industrially advantageous. In addition, even when the ester or the lactone to be reduced is labile to a base, the ester and the lactone can be reduced to alcohols without unnecessary chemical conversion such as decomposition and polymerization. Moreover, even when the ester or the lactone is an optically active substance, the ester and the lactone can be reduced to alcohols without lowering the optical purity. Furthermore, since a catalyst can be prepared easily, the method of the present invention is industrially advantageous.

DESCRIPTION OF THE PREFERRED EMBODIMENTS

Hereinbelow, the present invention will be described in detail.

In the present invention, an ester or a lactone is used as a material of a hydrogenation substrate. Examples of the ester used as the hydrogenation substrate include aliphatic carboxylic acid esters and aromatic carboxylic acid esters. The ester may derive from monocarboxylic acids or polycarboxylic acids. These esters and lactones may have any substituent as long as the substituent does not adversely affect the hydrogenation process of the present invention.

In the present invention, examples of the esters used as the hydrogenation substrate include alkyl esters, aryl esters, aralkyl esters, cycloalkyl esters, and the like of aliphatic carboxylic acids or aromatic carboxylic acids as follows.

Examples of the aliphatic carboxylic acids include: mono- and polycarboxylic acids having a linear or cyclic aliphatic group with 2 to 50 carbon atoms, preferably 2 to 20 carbon atoms, and more preferably 2 to 14 carbon atoms; and mono- and polycarboxylic acids having a 3- to 8-membered (preferably, O-5 to 6-membered) monocyclic, polycyclic, or condensed aliphatic heterocyclic group with 2 to 14 carbon atoms and at least one heteroatom (preferably 1 to 3 heteroatoms) such as a nitrogen atom, an oxygen atom and/or a sulfur atom. Specific examples thereof include acetic acid, propionic acid, butyric acid, valeric acid, hexanoic acid, heptanoic acid, octanoic acid, nonanoic acid, decanoic acid, dodecanoic acid, lauric acid, myristic acid, palmitic acid, stearic acid, oleic acid, oxalic acid, propanedicarboxylic acid, butanedicarboxylic acid, hexanedicarboxylic acid, sebacic acid, acrylic acid, cyclopentanecarboxylic acid, cyclohexanecarboxylic acid, cyclopentenecarboxylic acid, cyclohexenecarboxylic acid, 2-azetidinecarboxylic acid, 2-pyrrolidinecarboxylic acid (proline), 3-pyrrolidinecarboxylic acid, 2-piperidinecarboxylic acid, 3-piperidinecarboxylic acid, 4-piperidinecarboxylic acid, and piperazine-2-carboxylic acid.

These aliphatic carboxylic acids may have a substituent. Examples of the substituent include an alkyl group, an aryl group, an aralkyl group, a cycloalkyl group, an alkoxy group, an aryloxy group, an aralkyloxy group, a halogen atom, a heterocyclic group, an optionally-protected amino group, and an optionally-protected hydroxy group.

An example of the alkyl group as the substituent in the aliphatic carboxylic acids is a linear or branched alkyl group with 1 to 50 carbon atoms, preferably 1 to 20 carbon atoms, and more preferably 1 to 10 carbon atoms. Specific examples thereof include a methyl group, an ethyl group, an n-propyl group, an isopropyl group, an n-butyl group, an isobutyl group, an s-butyl group, a t-butyl group, an n-pentyl group, an n-hexyl group, and an n-octyl group.

An example of the aryl group as the substituent in the aliphatic carboxylic acids is a monocyclic, polycyclic, or condensed aryl group with 6 to 36 carbon atoms, preferably 6 to 18 carbon atoms, and more preferably 6 to 14 carbon atoms. Specific examples thereof include a phenyl group, a naphthyl group, an anthryl group, a phenanthryl group, and a biphenyl group.

An example of the aralkyl group as the substituent in the aliphatic carboxylic acids is a group in which at least one hydrogen atom of the alkyl group is replaced with the aryl group. The aralkyl group preferably has, for example, 7 to 15 carbon atoms. Specific examples thereof include a benzyl group, a 1-phenylethyl group, a 2-phenylethyl group, a 1-phenylpropyl group, and a 3-naphthylpropyl group.

An example of the cycloalkyl group as the substituent in the aliphatic carboxylic acids is a monocyclic, polycyclic, or condensed cycloalkyl group with 3 to 30 carbon atoms, preferably 3 to 20 carbon atoms, and more preferably 3 to 10 carbon atoms. Specific examples thereof include a cyclopropyl group, a cyclopentyl group, and a cyclohexyl group.

An example of the alkoxy group as the substituent in the aliphatic carboxylic acids is an alkoxy group in which a linear, branched, or cyclic alkyl group or cycloalkyl group with 1 to 20 carbon atoms (preferably 1 to 15 carbon atoms, and more preferably 1 to 10 carbon atoms (if cyclic, at least 3 carbon atoms)) is bonded to an oxygen atom. Specific examples thereof include a methoxy group, an ethoxy group, an n-propoxy group, an isopropoxy group, an n-butoxy group, an isobutoxy group, an s-butoxy group, a t-butoxy group, an n-pentyloxy group, an n-hexyloxy group, an n-octyloxy group, a cyclopentyloxy group, and a cyclohexyloxy group.

An example of the aryloxy group as the substituent in the aliphatic carboxylic acids is an aryloxy group in which a monocyclic, polycyclic, or condensed aryl group with 6 to 36 carbon atoms (preferably 6 to 18 carbon atoms, and more preferably 6 to 14 carbon atoms) is bonded to an oxygen atom. Specific examples thereof include a phenoxy group, a tolyloxy group, a xylyloxy group, and a naphthoxy group.

An example of the aralkyloxy group as the substituent in the aliphatic carboxylic acids is a group in which at least one hydrogen atom of the alkyl group or the cycloalkyl group in the alkoxy group is replaced with the aryl group. The aralkyloxy group preferably has, for example, 7 to 15 carbon atoms. Specific examples thereof include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, and a 2-naphthylmethoxy group.

Examples of the halogen atom as the substituent in the aliphatic carboxylic acids include fluorine, chlorine, bromine, and iodine.

Examples of the heterocyclic group as the substituent in the aliphatic carboxylic acids include an aliphatic heterocyclic group and an aromatic heterocyclic group. An example of the aliphatic heterocyclic group is, for example, a 3- to 8-membered (preferably, 4- to 6-membered) monocyclic, polycyclic, or condensed aliphatic heterocyclic group with 2 to 14 carbon atoms and at least one heteroatom (preferably, 1 to 3 heteroatoms) such as a nitrogen atom, an oxygen atom and/or a sulfur atom. Specific examples of the aliphatic heterocyclic group include an azetidyl group, an azetidino group, a pyrrolidyl group, a pyrrolidino group, a piperidinyl group, a piperidino group, a piperazinyl group, a piperazino group, a morpholinyl group, a morpholino group, a tetrahydrofuryl group, a tetrahydropyranyl group, and a tetrahydrothiophenyl group. Meanwhile, an example of the aromatic heterocyclic group is, for example, a 3- to 8-membered (preferably, 5- or 6-membered) monocyclic, polycyclic, or condensed heteroaryl group with 2 to 15 carbon atoms and at least one heteroatom (preferably, 1 to 3 heteroatoms) such as a nitrogen atom, an oxygen atom and/or a sulfur atom. The specific examples thereof include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzimidazolyl group, a benzoxazolyl group, a benzothiazolyl group, an acridyl group, and an acridinyl group.

Examples of the optionally-protected amino group as the substituent in the aliphatic carboxylic acids include: unprotected amino groups; mono- and di-alkylamino groups such as a N-methylamino group, a N,N-dimethylamino group, a N,N-diethylamino group, a N,N-diisopropylamino group, and a N-cyclohexylamino group; mono- and di-arylamino groups such as a N-phenylamino group, a N,N-diphenylamino group, a N-naphthylamino group, and a N-naphthyl-N-phenylamino group; mono- and di-aralkylamino groups such as a N-benzylamino group and a N,N-dibenzylamino group; acylamino groups such as a formylamino group, an acetylamino group, a propionylamino group, a pivaloylamino group, a pentanoylamino group, a hexanoylamino group, and a benzoylamino group; alkoxycarbonylamino groups such as a methoxycarbonylamino group, an ethoxycarbonylamino group, an n-propoxycarbonylamino group, an n-butoxycarbonylamino group, a tert-butoxycarbonylamino group, a pentyloxycarbonylamino group, and a hexyloxycarbonylamino group; aryloxycarbonylamino groups such as a phenyloxycarbonylamino group; and aralkyloxycarbonylamino groups such as a benzyloxycarbonylamino group. Other examples of the optionally-protected amino group include those protected by common protective groups for the amino group described in, for example, Reference Document 1 (Protective Groups in Organic Synthesis; Second Edition, JOHN WIREY & SONS, INC. 1991).

Furthermore, examples of the optionally-protected hydroxy group as the substituent in the aliphatic carboxylic acids include unprotected hydroxy groups and hydroxy groups that may be protected by common protective groups for hydroxy groups which are described in, for example, Reference Document 1, and which includes, for example, a methoxymethyl group, a benzyl group, and silyl groups such as trialkylsilyl groups (a trimethylsilyl group, a t-butyldimethylsilyl group, and the like). Note that, when the protective group is an acyl group, a resultant product may have the protective group reduced.

The alkyl group, the aryl group, the aralkyl group, the cycloalkyl group, the alkoxy group, the aralkyloxy group, the aryloxy group, and the heterocyclic group, which are listed as the substituent in the aliphatic carboxylic acids, may also have a substituent such as an alkyl group, an aryl group, an aralkyl group, a cycloalkyl group, an alkoxy group, an aralkyloxy group, an aryloxy group, a halogen atom, a heterocyclic group, an optionally-protected amino group, and an optionally-protected hydroxy group, which have been described above.

Examples of the aromatic carboxylic acids include: monocyclic, polycyclic, or condensed aryl groups with 6 to 36 carbon atoms, preferably 6 to 18 carbon atoms, and more preferably 6 to 12 carbon atoms; and mono- and polyaromatic carboxylic acids having a 3- to 8-membered (preferably, 5- to 8-membered) monocyclic, polycyclic, or condensed heteroaryl group with 1 to 4 heteroatoms (preferably 1 to 3 heteroatoms, more preferably 1 to 2 heteroatoms) such as a nitrogen atom, an oxygen atom, and a sulfur atom. Specific examples thereof include benzoic acid, naphthalenecarboxylic acid, pyridinecarboxylic acid, pyridinedicarboxylic acid, quinolinecarboxylic acid, furancarboxylic acid, and thiophenecarboxylic acid.

These aromatic carboxylic acids may also have a substituent such as an alkyl group, an aryl group, an aralkyl group, a cycloalkyl group, an alkoxy group, an aryloxy group, an aralkyloxy group, a halogen atom, a heterocyclic group, an optionally-protected amino group, and an optionally-protected hydroxy group, which have been described as the substituent in the aliphatic carboxylic acids.

On the other hand, examples of the lactones used in the present invention include β-lactone, γ-lactone, and δ-lactone. These lactones may have a substituent such as an alkyl group, an aryl group, an aralkyl group, a cycloalkyl group, an alkoxy group, an aryloxy group, an aralkyloxy group, a halogen atom, a heterocyclic group, an optionally-protected amino group, and an optionally-protected hydroxy group, which have been described as the substituent in the aliphatic carboxylic acids. Moreover, the lactones may have a bicyclo-ring structure or a condensed structure with an aromatic ring.

Meanwhile, examples of alkyl groups in the alkyl esters, aryl groups in the aryl esters, aralkyl groups in the aralkyl esters, and cycloalkyl groups in the cycloalkyl esters respectively include those that have been described as the substituents in the aliphatic carboxylic acids. Furthermore, these groups may have a substituent such as an alkyl group, an aryl group, an aralkyl group, a cycloalkyl group, an alkoxy group, an aralkyloxy group, an aryloxy group, a halogen atom, a heterocyclic group, an optionally-protected amino group, and an optionally-protected hydroxy group, which have been described as the substituent in the aliphatic carboxylic acids.

Preferable examples of the esters include alkyl esters with 1 to 10 carbon atoms, and preferably 1 to 5 carbon atoms, such as methyl ester, ethyl ester, and isopropyl ester. A more preferable example of the esters is methyl ester.

Each of these esters does not necessarily have to have an asymmetric center. The ester may be an optically active substance or a mixture of various isomers.

The alcohol production method of the present invention is suitably performed without a solvent or in a solvent. However, it is preferable to use a solvent. The solvent is preferably capable of dissolving the substrate and the catalyst. A single solvent or a mixed solvent is used. Specific examples thereof include: aromatic hydrocarbons such as toluene and xylene; aliphatic hydrocarbons such as hexane and heptane; halogenated hydrocarbons such as dichloromethane and chlorobenzene; ethers such as diethyl ether, tetrahydrofuran, methyl t-butyl ether, and cyclopentyl methyl ether; alcohols such as methanol, ethanol, isopropanol, n-butanol, and 2-butanol; and polyvalent alcohols such as ethylene glycol, propylene glycol, 1,2-propanediol and glycerin. Among them, ethers are preferable, and tetrahydrofuran is particularly preferable, as the solvent. The amount of the solvent can be appropriately selected, depending on reaction conditions and the like. The reaction is conducted with stirring as necessary.

The amount of the catalyst differs, depending on the hydrogenation substrate, the reaction conditions, the type of the catalyst, and the like. However, the molar ratio of a ruthenium metal to the hydrogenation substrate is normally in the range of 0.001 mol % to 10 mol %, and preferably 0.05 mol % to 5 mol %.

In the method of the present invention, the reaction temperature at the time of hydrogen reduction is 50° C. to 150° C., and preferably 60° C. to 120° C. If the reaction temperature is too low, a large amount of the material may remain unreacted. Meanwhile, if the reaction temperature is too high, the material, the catalyst, and the like may decompose. Thus, such extreme conditions are not favorable.

In the present invention, the hydrogen pressure at the time of hydrogen reduction is 1 MPa to 10 MPa, and preferably 3 MPa to 6 MPa.

The reaction time of approximately 2 hours to 20 hours allows obtaining a sufficiently high material conversion rate.

After the reaction is completed, normally-used purification techniques such as extraction, filtration, crystallization, distillation, and various chromatography techniques are performed singly or in combination as appropriate. In this manner, a targeted alcohol can be obtained.

In the present invention, specific examples of an organic base compound in a base compound include amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine, and N-methylmorpholine.

Meanwhile, specific examples of an inorganic base compound in the base compound include: alkali metal carbonates such as potassium carbonate, sodium carbonate, lithium carbonate, and cesium carbonate; alkaline earth metal carbonates such as magnesium carbonate and calcium carbonate; alkali metal bicarbonates such as sodium bicarbonate and potassium bicarbonate; alkali metal hydroxides such as sodium hydroxide, potassium hydroxide, and lithium hydroxide; alkaline earth metal hydroxides such as magnesium hydroxide and calcium hydroxide; alkali metal alkoxides such as sodium methoxide, sodium ethoxide, sodium isopropoxide, sodium t-butoxide, potassium methoxide, potassium ethoxide, potassium isopropoxide, potassium t-butoxide, lithium methoxide, lithium isopropoxide, and lithium t-butoxide; alkaline earth metal alkoxides such as magnesium methoxide and magnesium ethoxide; and metal hydrides such as sodium hydride and calcium hydride.

A ruthenium compound is used as a starting material for producing a ruthenium complex used in the present invention. Examples of the ruthenium compound include: inorganic ruthenium compounds such as $RuCl_3$ hydrate, $RuBr_3$ hydrate, and $RuI_3$ hydrate; and $RuCl_2(DMSO)_4$, $[Ru(cod)Cl_2]_n$, $[Ru(nbd)Cl_2]_n$, $(COD)Ru(2\text{-methallyl})_2$, $[Ru(benzene)Cl_2]_2$, $[Ru(benzene)Br_2]_2$, $[Ru(benzene)I_2]_2$, $[Ru(p\text{-cymene})Cl_2]_2$, $[Ru(p\text{-cymene})Br_2]_2$, $[Ru(p\text{-cymene})I_2]_2$, $[Ru(mesitylene)Cl_2]_2$, $[Ru(mesitylene)Br_2]_2$, $[Ru(mesitylene)I_2]_2$, $[Ru(hexamethylbenzene)Cl_2]_2$, $[Ru(hexamethylbenzene)Br_2]_2$, $[Ru(hexamethylbenzene)I_2]_2$, $RuCl_2(PPh_3)_3$, $RuBr_2(PPh_3)_3$, $RuI_2(PPh_3)_3$, $RuH_4(PPh_3)_3$, $RuClH(PPh_3)_3$, $RuH(OAc)(PPh_3)_3$, and $RuH_2(PPh_3)_4$. In the above examples, DMSO represents dimethylsulfoxide, cod represents 1,5-cyclooctadiene, nbd represents norbornadiene, and Ph represents a phenyl group.

Next, a ruthenium complex used as the catalyst in the present invention will be described. The ruthenium complex is represented by the following general formula (1):

$$RuH(X)(L^1)(L^2)_n \qquad (1)$$

wherein X represents a monovalent anionic ligand; $L^1$ represents a tetradentate ligand having at least one coordinating phosphino group and at least one coordinating amino group or a bidentate aminophosphine ligand having one coordinating phosphino group and one coordinating amino group; $L^2$ represents a bidentate aminophosphine ligand having one coordinating phosphino group and one coordinating amino group, provided that n is 0 when $L^1$ is the tetradentate ligand, and n is 1 when $L^1$ is the bidentate ligand.

First, the monovalent anionic ligand represented by X in the general formula (1) will be described. Examples of the monovalent anionic ligand include a hydrogen atom (hydride), $AlH_4$, $BH_4$, ligands represented by the following general formulae (8), (9a) and (9b), a halogen atom, an alkoxy group, an aryloxy group, an aralkyloxy group, a hydroxy group, an acyloxy group, and a sulfonyloxy group.

(8)

$MH_rR^{25}_{(4-r)}$

(9a)

(9b)

wherein M represents aluminium or boron; r is a natural number between 0 to 3 inclusive; $R^{25}$ represents an alkyl group which may have a substituent, an aryl group which may have a substituent, an aralkyl group which may have a substituent, a cycloalkyl group which may have a substituent, an alkoxy group which may have a substituent, an aryloxy group which may have a substituent, or an aralkyloxy group which may have a substituent; $R^{26}$ and $R^{26'}$, which may be same or different, each represent a hydrogen atom, an alkyl group which may have a substituent, an aryl group which may have a substituent, an aralkyl group which may have a substituent, or a cycloalkyl group which may have a substituent; $R^{26}$ and another $R^{26}$, or $R^{26}$ and $R^{26'}$ may bond to each other to form a ring; and $Q^{9a}$ and $Q^{9b}$ each independently represent a divalent arylene group which may have a substituent or an alkylene group which may have a substituent.

Here, the alkyl group, the aryl group, the aralkyl group, the cycloalkyl group, the alkoxy group, the aryloxy group, and the aralkyloxy group are the same as those that have been described as the substituent in the aliphatic carboxylic acids. Examples of the substituents which these groups may have include an alkyl group, an aryl group, an aralkyl group, a cycloalkyl group, an alkoxy group, an aralkyloxy group, an aryloxy group, a halogen atom, a heterocyclic group, an optionally-protected amino group, an optionally-protected hydroxy group, and the like, which have been described as the substituent in the aliphatic carboxylic acids.

An example of the divalent arylene groups represented by $Q^{9a}$ and $Q^{9b}$ is a divalent group which is composed of a monocyclic or condensed aryl group with 6 to 12 carbon atoms. Examples of the divalent group include a phenylene group and a 2,3-naphthalenediyl group. Examples of the phenylene group include an o-phenylene group and an m-phenylene group. An example of the alkylene group is a linear or branched alkyl group with 1 to 20 carbon atoms, preferably 1 to 10 carbon atoms, and more preferably 1 to 6 carbon atoms. Specific examples thereof include a methylene group, an ethylene group, a trimethylene group, a tetramethylene group, and a pentamethylene group. Furthermore, the alkylene group may be a cycloalkylene group. An example of the cycloalkylene group is a divalent group composed of a monocyclic, polycyclic, or condensed cycloalkyl group with 3 to 15 carbon atoms, preferably 3 to 10 carbon atoms, and more preferably 3 to 6 carbon atoms. Specific examples thereof include a cyclopropylene group, a cyclobutylene group, a cyclopentylene group, and a cyclohexylene group. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids.

The alkyl group, the aryl group, the aralkyl group, the cycloalkyl group, the alkoxy group, the aryloxy group, the aralkyloxy group, and the heterocyclic group may have a substituent that has been described, such as an alkyl group, an aryl group, an aralkyl group, a cycloalkyl group, an alkoxy group, an aryloxy group, an aralkyloxy group, a halogen atom, a heterocyclic group, an optionally-protected amino group, and an optionally-protected hydroxy group. Examples of $Q^{9a}$ and $Q^{9b}$ include a 2,2,2-trifluoroethoxy group, a 1,1,1,3,3,3-hexafluoro-2-propoxy group, a 1-pentafluorophenylethoxy group, and a pentafluorophenoxy group. The monovalent anionic ligand of the general formulae (9a) and (9b) may be represented by the following structural formulae 9A and 9B.

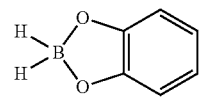

9A

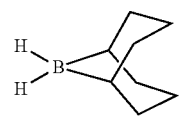

9B

The acyloxy group may be represented by ($R^aCO_2$). Examples of $R^a$ in the acyloxy group $R^aCO_2$ include a hydrogen atom, an alkyl group, an aryl group, an aralkyl group, and a cycloalkyl group. The alkyl group, the aryl group, the aralkyl group, and the cycloalkyl group are the same as those that have been described as the substituent in the aliphatic carboxylic acids. These groups may further have a substituent such as an alkyl group, an aryl group, an aralkyl group, a cycloalkyl group, an alkoxy group, an aralkyloxy group, an aryloxy group, a halogen atom, a heterocyclic group, an optionally-protected amino group, and an optionally-protected hydroxy group, which have been described as the substituent in the aliphatic carboxylic acids. Specific examples of $R^a$ include a methyl group, an ethyl group, a propyl group, a t-butyl group, a trifluoromethyl group, a phenyl group, and a pentafluorophenyl group.

The sulfonyloxy group may be represented by ($R^SSO_3$). Examples of the $R^S$ in the sulfonyloxy group $R^SSO_3$ are the same as those of $R^a$ in the acyloxy group.

The ruthenium complex represented by the general formula (1) can be obtained by methods described in, for example, Chem. Eur. J. 2003, 9, 4954, Adv. Synth. Catal. 2005, 347, 571, and the like. The complex thus prepared may have its stereoisomer due to the coordination and conformation of the ligands. The complex used in the present reaction may be a mixture of such stereoisomers or a single pure isomer.

In addition, according to the methods described in, for example, J. Am. Chem. Soc. 2005, 127, 516 and Organomet. 2007, 26, 5940 described above, a ruthenium hydride complex represented by the general formula (1) wherein X=$BH_4$ can be obtained. Such complexes exist relatively stably, and are relatively easy to handle.

Next, the tetradentate ligand which is represented by $L^1$ in the general formula (1), and which is used in the present invention, will be described. The tetradentate ligand is preferably a ligand having at least one coordinating phosphino group and at least one coordinating amino group, and more preferably a ligand further having one coordinating phosphorus atom and one coordinating nitrogen atom, and most preferably an aminophosphine ligand having two coordinating phosphino groups and two coordinating amino groups.

Specifically, the tetradentate ligand may be represented by, for example, the following general formula (2):

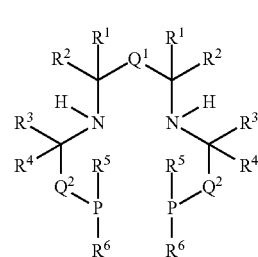

(2)

wherein $R^1$, $R^2$, $R^3$, $R^4$, $R^5$ and $R^6$, which may be same or different, each represent a hydrogen atom, an alkyl group which may have a substituent, an aralkyl group which may have a substituent, an aryl group which may have a substituent, or a cycloalkyl group which may have a substituent; $R^1$ and another $R^1$, $R^1$ and either $R^2$, $R^3$ or $R^4$, $R^3$ and $R^4$, or $R^5$ and $R^6$ may bond to each other to form a ring; and $Q^2$ and $Q^2$, which may be same or different, each represent a divalent arylene group which may have a substituent, an alkylene group which may have a substituent, or a bond.

The alkyl group, the aryl group, the aralkyl group, and the cycloalkyl group represented by $R^1$, $R^2$, $R^3$, $R^4$, $R^5$ and $R^6$ in the formula are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids.

An example of the divalent arylene groups represented by $Q^2$ and $Q^2$ is a divalent group which is composed of a monocyclic or condensed aryl group with 6 to 12 carbon atoms. Examples thereof include a phenylene group and a 2,3-naphthalenediyl group. Examples of the phenylene group include an o-phenylene group and an m-phenylene group. An example of the alkylene group is a linear or branched alkyl group with 1 to 20 carbon atoms, preferably 1 to 10 carbon atoms, and more preferably 1 to 6 carbon atoms. Specific examples thereof include a methylene group, an ethylene group, a trimethylene group, a tetramethylene group, and a pentamethylene group. Furthermore, the alkylene group may be a cycloalkylene group. An example of the cycloalkylene group is a divalent group composed of a monocyclic, polycyclic, or condensed cycloalkyl group with 3 to 15 carbon atoms, preferably 3 to 10 carbon atoms, and more preferably 3 to 6 carbon atoms. Specific examples of the divalent group include a cyclopropylene group, a cyclobutylene group, a cyclopentylene group, and a cyclohexylene group. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids.

The ligand represented by the general formula (2) does not necessarily have to be an optically active substance. The ligand may be an optically active substance, a racemic body, or a mixture of various stereoisomers, depending on $Q^1$, $Q^2$, $R^1$, $R^2$, $R^3$, $R^4$, $R^5$ and $R^6$.

Next, the bidentate ligands used in the present invention will be described.

The bidentate ligands represented by $L^1$ and $L^2$ in the general formula (1) are each preferably an aminophosphine ligand having a coordinating phosphorus atom and a coordinating nitrogen atom.

Specifically, the bidentate ligand may be represented by, for example, the following general formula (3).

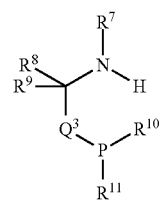

(3)

wherein $R^7$, $R^8$, $R^9$, $R^{20}$ and $R^{11}$, which may be same or different, each represent a hydrogen atom, an alkyl group which may have a substituent, an aryl group which may have a substituent, an aralkyl group which may have a substituent, or an cycloalkyl group which may have a substituent; $R^7$ and $R^8$ or $R^9$, $R^8$ and $R^9$, or $R^{10}$ and $R^{11}$ may bond to each other to form a ring; and $Q^3$ represents a divalent arylene group which may have a substituent, an alkylene group which may have a substituent, or a bond.

In the general formula (3), $R^7$, $R^8$, $R^9$, $R^{10}$ and $R^{11}$ are the same as $R^1$, $R^2$, $R^3$, $R^4$, $R^5$ and $R^6$ in the general formula (2) described above. Likewise, $Q^3$ in the general formula (3) is the same as $Q^1$ and $Q^2$ in the general formula (2) described above.

The ligand represented by the general formula (3) does not necessarily have to be an optically active substance. The ligand may be an optically active substance, a racemic body, or a mixture of various stereoisomers, depending on $Q^3$, $R^7$, $R^8$, $R^9$, $R^{20}$ and $R^{11}$.

Next, a tetradentate ligand which has an imine structure, and which is used in the present invention, will be described. The tetradentate ligand is represented by a general formula (4) or (5):

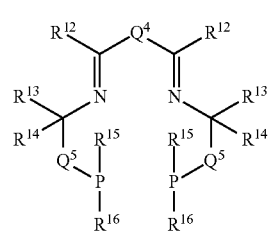

(4)

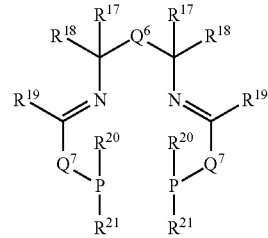

(5)

wherein $R^{12}$, $R^{13}$, $R^{14}$, $R^{15}$, $R^{16}$, $R^{17}$, $R^{18}$, $R^{19}$, $R^{20}$ and $R^{21}$, which may be same or different, each represent a hydrogen atom, an alkyl group which may have a substituent, an aryl group which may have a substituent, an aralkyl group which may have a substituent, or a cycloalkyl group which may have a substituent; $R^{12}$ and another $R^{12}$, $R^{12}$ and $R^{13}$ or $R^{14}$, $R^{13}$ and $R^{14}$, $R^{15}$ and $R^{16}$, $R^{17}$ and another $R^{17}$, $R^{19}$ and $R^{17}$ or $R^{18}$, or $R^{20}$ and $R^{21}$ may bond to each other to form a ring; and $Q^4$, $Q^5$, $Q^6$ and $Q^7$, which may be same or different, each represent a divalent arylene group which may have a substituent, an alkylene group which may have a substituent, or a bond.

In the general formulae (4) and (5), $R^{12}$, $R^{13}$, $R^{14}$, $R^{15}$, $R^{16}$, $R^{17}$, $R^{18}$, $R^{19}$, $R^{20}$ and $R^{21}$ are the same as $R^1$, $R^2$, $R^3$, $R^4$, $R^5$, and $R^6$ in the general formula (2). Likewise, $Q^4$, $Q^5$, $Q^6$ and $Q^7$ in the general formulae (4) and (5) are the same as $Q^1$ and $Q^2$ in the general formula (2).

Next, a bidentate ligand which has an imine structure, and which is used in the present invention, will be described. The bidentate ligand is represented by general formulae (7a) and (7b).

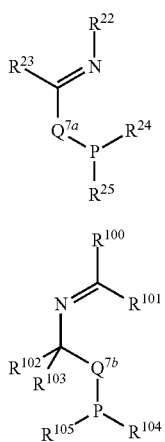

wherein $R^{22}$, $R^{23}$, $R^{24}$, $R^{25}$, $R^{100}$, $R^{101}$, $R^{102}$, $R^{103}$, $R^{104}$ and $R^{105}$, which may be same or different, each represent a hydrogen atom, an alkyl group which may have a substituent, an aryl group which may have a substituent, an aralkyl group which may have a substituent, or a cycloalkyl group which may have a substituent; $R^{22}$ and $R^{23}$, $R^{24}$ and $R^{25}$, or $R^{104}$ and $R^{105}$ may bond to each other to form a ring; and $Q^{7a}$ and $Q^{7b}$ each represent a divalent arylene group which may have a substituent, an alkylene group which may have a substituent, or a bond.

In the general formulae (7a) and (7b), $R^{22}$, $R^{23}$, $R^{24}$, $R^{25}$, $R^{100}$, $R^{101}$, $R^{102}$, $R^{103}$, $R^{104}$ and $R^{105}$ are the same as $R^1$, $R^2$, $R^3$, $R^4$, $R^5$ and $R^6$ in the general formula (2). Likewise, $Q^{7a}$ and $Q^{7b}$ in the general formulae (7a) and (7b) are the same as $Q^1$ and $Q^2$ in the general formula (2).

Next, the ruthenium complexes used as the catalyst in the present invention will be described. The ruthenium complexes are represented by general formulae (6) and (6'):

$$[Ru(X^1)_k(X^2)_l(Y^1)_m(Y^2)_o(L^{1'})](Z)_q \qquad (6)$$

$$[Ru(X^3)_k(X^4)_{l'}(Y^3)_{m'}(Y^4)_{o'}(L^{1''})(L^{2''})](Z')_{q'} \qquad (6')$$

wherein $X^1$, $X^2$, $X^3$ and $X^4$ each independently represent a monovalent anionic ligand; $Y^1$, $Y^2$, $Y^3$ and $Y^4$ each independently represent a neutral monodentate ligand; Z and Z' each represent a monovalent anion that does not coordinate to a metal; $L^{1'}$ represents the tetradentate ligand represented by the general formula (4) or (5); $L^{1''}$ and $L^{2''}$, which may be same or different, each represent the bidentate ligand represented by the general formula (7a) or (7b), provided that: k, l, m and o are each a natural number between 0 to 2 inclusive, and satisfy $0 \le k+l+m+o \le 2$; q is 0 when k+l=2, q is 1 when k+l=1, and q is 2 when k+l=0; k', l', m' and o' are each a natural number between 0 to 2 inclusive, and satisfy $0 \le k'+l'+m'+o' \le 2$; and q' is 0 when k'+l'=2, q' is 1 when k'+l'=1, and q' is 2 when k'+l'=0.

In the general formulae (6) and (6'), $X^1$, $X^2$, $X^3$ and $X^4$ are the same as X in the general formula (1). Examples of $Y^1$, $Y^2$, $Y^3$ and $Y^4$ in the general formulae (6) and (6') include water, alcohols, ethers, amines, amides, nitriles, sulfides, sulfoxides, phosphines, and phosphine oxides.

The alcohols may be represented by, for example, the following general formula (10):

$$R^{27}\text{—OH} \qquad (10)$$

wherein $R^{27}$ represents an alkyl group which may have a substituent, an aralkyl group which may have a substituent, an aryl group which may have a substituent, or a cycloalkyl group which may have a substituent.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids.

Preferable examples of the alcohols are lower alcohols with 1 to 4 carbon atoms. More specific examples thereof include methanol, ethanol, n-propanol, isopropanol, n-butanol, sec-butanol, tert-butanol, 2,2,2-trifluoroethanol, and 1,1,1,3,3,3-hexafluoro-2-propanol.

The ethers may be represented by, for example, the following general formula (11):

$$R^{28}\text{—O—}R^{29} \qquad (11)$$

wherein $R^{28}$ and $R^{29}$, which may be same or different, each represent an alkyl group which may have a substituent, an aralkyl group which may have a substituent, an aryl group which may have a substituent, or a cycloalkyl group which may have a substituent; alternatively, $R^{28}$ and $R^{29}$ may bond to each other to form a cyclic ether.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the ethers include cyclic and acyclic ethers with 2 to 12 carbon atoms. More specific examples thereof include diethyl ether, diisopropyl ether, tert-butyl methyl ether, cyclopentyl methyl ether, tetrahydrofuran, and 1,4-dioxane.

The amines may be represented by, for example, the following general formula (12):

$$R^{30}R^{31}R^{32}N \qquad (12)$$

wherein $R^{30}$, $R^{31}$ and $R^{32}$, which may be same or different, each represent a hydrogen atom, an alkyl group which may have a substituent, an aralkyl group which may have a substituent, an aryl group which may have a substituent, or a cycloalkyl group which may have a substituent; alternatively, $R^{30}$ and $R^{31}$ and/or $R^{32}$ may bond to each other to form a ring.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the amines include aliphatic and aromatic amines such as triethylamine, tri-n-butylamine, triphenylamine, pyridine, dimethylaminopyridine, and pyrimidine.

The amides may be represented by, for example, the following general formula (13):

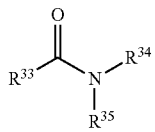
(13)

wherein $R^{33}$, $R^{34}$ and $R^{35}$, which may be same or different, each represent a hydrogen atom, an alkyl group which may have a substituent, an aralkyl group which may have a substituent, an aryl group which may have a substituent, or a cycloalkyl group which may have a substituent; alternatively, $R^{33}$ and $R^{34}$ and/or $R^{35}$ may bond to each other to form a ring.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the amides include dimethylformamide, dimethylacetamide, and benzamide.

The nitriles may be represented by, for example, the following general formula (14):

$$R^{36}\text{—CN} \quad (14)$$

wherein $R^{36}$ represents an alkyl group which may have a substituent, an aralkyl group which may have a substituent, an aryl group which may have a substituent, or a cycloalkyl group which may have a substituent.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the nitriles include acetonitrile and benzonitrile.

The sulfides may be represented by, for example, the following general formula (15):

$$R^{37}\text{—S—}R^{38} \quad (15)$$

wherein $R^{37}$ and $R^{38}$, which may be same or different, each represent an alkyl group which may have a substituent, an aralkyl group which may have a substituent, an aryl group which may have a substituent, or a cycloalkyl group which may have a substituent; alternatively, $R^{37}$ and $R^{38}$ may bond to each other to form a ring.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the sulfides include dimethylsulfide, tetrahydrothiophene, thioanisole, and thiophene.

The sulfoxides may be represented by, for example, the following general formula (16):

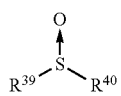
(16)

wherein $R^{39}$ and $R^{40}$, which may be same or different, each represent an alkyl group which may have a substituent, an aralkyl group which may have a substituent, an aryl group which may have a substituent, or a cycloalkyl group which may have a substituent; alternatively, $R^{39}$ and $R^{49}$ may bond to each other to form a ring.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the sulfoxides include dimethylsulfoxide and tetramethylenesulfoxide.

The phosphines may be represented by, for example, the following general formula (17):

$$R^{41}R^{42}R^{43}P \quad (17)$$

wherein $R^{41}$, $R^{42}$ and $R^{43}$, which may be same or different, each represent a hydrogen atom, an alkyl group which may have a substituent, an aralkyl group which may have a substituent, an aryl group which may have a substituent, or a cycloalkyl group which may have a substituent; alternatively, $R^{41}$ and $R^{42}$ and/or $R^{43}$ may bond to each other to form a ring.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the phosphines include triphenylphosphine, tritolylphosphine, trimethylphosphine, triethylphosphine, methyldiphenylphosphine, and dimethylphenylphosphine.

The phosphine oxides may be represented by, for example, the following general formula (18):

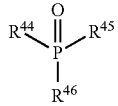 (18)

wherein $R^{44}$, $R^{45}$ and $R^{46}$, which may be same or different, each represent a hydrogen atom, an alkyl group which may have a substituent, an aralkyl group which may have a substituent, an aryl group which may have a substituent, or a cycloalkyl group which may have a substituent; alternatively, $R^{44}$ and $R^{45}$ and/or $R^{46}$ may bond to each other to form a ring.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aryloxy group, an aralkyloxy group, a halogen atom, a heterocyclic group, an optionally-protected amino group, an optionally-protected hydroxy group, and the like, which have been described as the substituent in the aliphatic carboxylic acids. Preferable examples of the phosphine oxides include oxides of the aforementioned phosphines.

Additionally, examples of Z and Z' in the general formulae (6) and (6') include anions of $BF_4$, $B(C_6F_5)_4$, $BPh_4$, $PF_6$, $ClO_4$, OTf, and the like. Here, Tf represents a trifluoromethanesulfonyl group.

Furthermore, a method of conducting the reaction with a complex obtained by reducing the ruthenium complex of the general formula (6) or (6') will be described. Examples of the reducing agent used in the method include: aluminium hydride compounds such as lithium aluminium hydride (LAH), lithium alkoxyaluminium hydrides represented by the following general formula (19), sodium bis (2-methoxyethoxy) aluminium hydride (Red-Al) diisobutylaluminium hydride (DIBAH); boron hydride compounds such as sodium borohydride, potassium borohydride, lithium borohydride, tetraalkylammonium borohydrides represented by the following general formula (20), zinc borohydride, sodium cyanoboronhydride, tetraalkylammonium cyanoborohydrides represented by the following general formula (21), lithium triethylborohydride (Super-Hydride) lithium tri(-sec-butyl)borohydride (L-Selectride), potassium tri(-sec-butyl) borohydride (K-Selectride), lithium 9-borabicyclo[3.3.1] nonane hydride (Li 9-BBN hydride), a borane-dimethyl sulfide complex, a borane-tetrahydrofuran complex, 9-borabicyclo[3.3.1]nonane (9-BBN) and catecholborane; and molecular hydrogen:

 (19)

 (20), and

 (21)

wherein $R^{47}$ represents an alkyl group which may have a substituent, an aralkyl group which may have a substituent, an aryl group which may have a substituent, or a cycloalkyl group which may have a substituent; $R^{48}$ and $R^{49}$ each represent an alkyl group which may have a substituent; and j represents a natural number between 1 to 3 inclusive.

Here, the alkyl group, the aryl group, the aralkyl group, and the cycloalkyl group are the same as those that have been described as the substituent in the aliphatic carboxylic acids. Examples of the substituents which these groups may have include an alkyl group, an aryl group, an aralkyl group, a cycloalkyl group, an alkoxy group, an aralkyloxy group, an aryloxy group, a halogen atom, a heterocyclic group, an optionally-protected amino group, an optionally-protected hydroxy group, and the like, which have been described as the substituent in the aliphatic carboxylic acids.

The ruthenium complex of the general formula (6) or (6') is reduced in a solvent. The solvent is a single solvent or a mixed solvent. Specific examples thereof include: aromatic hydrocarbons such as toluene and xylene; aliphatic hydrocarbons such as hexane and heptane; halogenated hydrocarbons such as dichloromethane and chlorobenzene; ethers such as diethyl ether, tetrahydrofuran, methyl t-butyl ether, and cyclopentyl methyl ether; alcohols such as methanol, ethanol, isopropanol, n-butanol, and 2-butanol; and polyvalent alcohols such as ethylene glycol, propylene glycol, 1,2-propanediol and glycerin. Among them, the solvent desirably contains primary or secondary alcohols. Particularly preferable solvents are methanol, ethanol, and a mixed solvent of toluene and these. The amount of the solvent can be appropriately selected, depending on reaction conditions and the like. The reaction is conducted with stirring as necessary.

Conventionally, the ruthenium hydride complex which is represented by the general formula (1) and which includes an aminophosphine ligand as represented by the general formula (2) or (3) has not been able to be obtained in a single step from a ruthenium complex including an iminophosphine ligand. In contrast, use of the method described in the present invention makes it possible to efficiently prepare the ruthenium hydride complex in fewer steps, and accordingly to simplify the production process.

Additionally, the complex obtained through the reduction step may be used as the catalyst without being isolated from the reaction solution.

By using such a ruthenium complex as the catalyst, alcohols can be produced from an ester and a lactone at high yield and at high catalytic efficiency under relatively low hydrogen pressure and reaction temperature which are industrially advantageous. Additionally, the ruthenium complex used in the present reaction catalyzes the reaction without adding a base. Thus, even when the ester or the lactone to be reduced is labile to a base, the ester and the lactone can be reduced to alcohols without undesirable side-reactions such as decomposition and polymerization. Moreover, even when the ester or the lactone is an optically active substance, the ester and the lactone can be reduced to alcohols without lowering the optical purity.

EXAMPLES

The present invention will be described in detail below with reference to the following non-limiting Examples and Comparative example.

Note that, $^1$H-NMR and $^{31}$P-NMR spectra were measured using MERCURY plus 300 manufactured by Varian, Inc. Additionally, the conversion rate, the selectivity and the optical purity were measured by gas chromatography (GC) and liquid chromatography (LC). The instruments used in the Examples are as follows.

A. Conversion rate and selectivity
A-1. Conversion rate-selectivity analysis condition A: used for analyses in Examples 1 to 5, 8, 11 to 15, 19, 20 and 23 and Comparative Examples 1 to 4
Capillary; HP-INNOWax
Injection temperature: 250° C., detection temperature: 250° C. 80° C. (1 min.) –10° C./min. –250° C. (12 min.)
A-2. Conversion rate-selectivity analysis condition B: used for analyses in Examples 9 and 10 and Comparative Example 10
GC; capillary RTx-5
Injection temperature: 250° C., detection temperature: 250° C. 80° C. (10 min.)–10° C./min.–270° C. (1 min.)
A-3. Conversion rate-selectivity analysis condition C: used for analyses in Examples 16 and 21
GC; capillary TC-FFAP
Injection temperature: 250° C., detection temperature: 250° C. 80° C.–5° C./min.–220° C. (2 min.)
B. Optical purity
B-1. Optical purity: optical purity analysis of 2-Boc-aminopropanol
The analysis was performed after the conversion into p-nitrobenzoate ester.
HPLC; Column DAICEL CHIRALCEL OD-H
Oven; 40° C., eluent; hexane:2-propanol=95:5
B-2. Optical purity: Example 8 and Comparative Example 9
HPLC; Column DAICEL CHIRALCEL OJ-H
Oven; 30° C., eluent; hexane:2-propanol=98:2
B-3. Optical purity: Optical purity analysis of 3-amino-1-butanol
The analysis was performed after the trifluoroacetylation of the amino group and the hydroxy group.
GC; capillary β-DEX225
Injection temperature: 250° C., detection temperature: 250° C. 160° C. (15 min.)
B-4. Optical purity: optical purity analysis of 1,2-propanediol
The analysis was performed after the trifluoroacetylation of the hydroxy group.
GC; capillary CHIRASIL-DEX-CB
Injection temperature: 250° C., detection temperature: 250° C. 45° C. (15 min.)–10° C./min.–125° C.
B-5. Optical purity: optical purity analysis of 1,3-butanediol
GC; capillary BETA-DEX™225
Injection temperature: 250° C., detection temperature: 250° C. 120° C. (30 min.)

Example 1

Synthesis of Ruthenium Complex 1 and Ester Reduction Using the Same

[RuClH(PPh₃)₃] (1.73 mmol) and $L^{1a}$ (1.73 mmol) were charged into a 100 mL-flask, and air inside the flask was replaced with nitrogen. Then, tetrahydrofuran (25 mL) was added to dissolve [RuClH(PPh₃)₃] and $L^{1a}$. After 1 hour of heating under reflux, most of the tetrahydrofuran was collected under reduced pressure. Thereafter, hexane (25 mL) was added, and a crystal was filtered and washed with hexane, tetrahydrofuran, and diethyl ether. The resultant crystal was dried under reduced pressure, and a ruthenium complex 2 (743 mg) was obtained.

$^1$H NMR (300 MHz, $C_6D_6$):
δ=–15.92 (t, J=27.2 Hz, 1H), 3.31 (m, 2H), 3.96 (m, 2H), 6.88-8.20 (m, 30H)
$^{31}$P NMR (121.5 MHz, $C_6D_6$):
δ=59.9 (d, J=22 Hz)

Under a stream of nitrogen, the ruthenium complex 2 (0.2 mmol) was suspended in toluene (20 mL). A solution of sodium borohydride (5.4 mmol) in ethanol (20 mL) was added, and the mixture was heated for 1 hour under reflux, then air-cooled, and concentrated under reduced pressure. After that, toluene (20 mL) was added, and the mixture was stirred for 30 minutes and celite-filtered. The celite was washed with toluene (20 mL). Under reduced pressure, most of the toluene was collected, and hexane (20 mL) was added. A deposited crystal was filtered. The crystal was washed with hexane, and thus a ruthenium complex 1 (80 mg) was obtained. The isomer ratio was 4:3 based on the area ratio of the hydride on the ruthenium according to H NMR.

The signals of the hydride on the ruthenium were as follows.
$^1$H NMR (300 MHz, $C_6D_6$)
Major isomer; δ –15.13 (dd, J=21.9 Hz, 25.8 Hz)
Minor isomer; δ –14.30 (t, J=26.1 Hz)
Meanwhile, the signals of $^{31}$PNMR were as follows.
$^{31}$PNMR (121.5 MHz, $C_6D_6$)
Major isomer; δ 66.4 (d, J=32 Hz), 64.7 (d, J=32 Hz)
Minor isomer; δ 65.4 (s)

The ruthenium complex 1 (0.0181 mmol) thus prepared was charged into a 100-mL autoclave equipped with a stirrer, and air inside the autoclave was replaced with nitrogen. Then, a solution of L-Boc-alanine methyl ester (3.16 mmol) in tetrahydrofuran (1.4 mL) was added thereinto. Then, the mixture was subjected to hydrogenation at a hydrogen pressure of 5 MPa at 80° C. for 16.0 hours. The reaction liquid was analyzed by gas chromatography. As a result, 2-Boc-aminopropanol was synthesized at a conversion rate of 68.0% and a selectivity of 97.4%.

Example 2

Hydrogenation of Methyl Benzoate

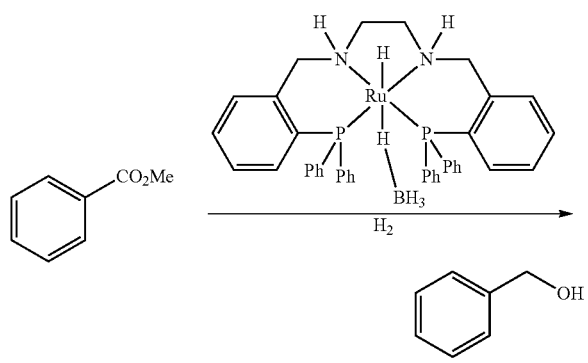

Methyl benzoate (7.99 mmol), a ruthenium complex 1 (0.004 mmol), and tetrahydrofuran (6 mL) were charged into a 100-mL autoclave equipped with a stirrer. Then, the mixture was subjected to hydrogenation at a hydrogen pressure of 5 MPa at 80° C. for 15.5 hours. The reaction liquid was analyzed by gas chromatography. As a result, benzyl alcohol was synthesized at a conversion rate of 96.2% and a selectivity of 86.7%.

Example 3

Hydrogenation of L-Boc-alanine Methyl Ester

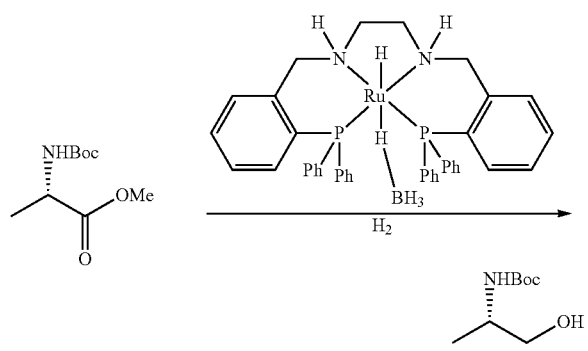

L-Boc-alanine methyl ester (2.46 mmol), a ruthenium complex 1 (0.005 mmol), and tetrahydrofuran (1 mL) were charged into a 100-mL autoclave equipped with a stirrer. Then, the mixture was subjected to hydrogenation at a hydrogen pressure of 5 MPa at 80° C. for 15.5 hours. The reaction liquid was analyzed by gas chromatography. As a result, 2-Boc-aminopropanol was synthesized at a conversion rate of 38.0% and a selectivity of 95.3%. The obtained alcohol had an optical purity of 98.8% ee.

Example 4

Hydrogenation of L-Boc-alanine Methyl Ester

L-Boc-alanine methyl ester (2.46 mmol), a ruthenium complex 1 (0.005 mmol), and tetrahydrofuran (1 mL) were charged into a 100-mL autoclave equipped with a stirrer. Then, the mixture was subjected to hydrogenation at a hydrogen pressure of 5 MPa at 100° C. for 16 hours. The reaction liquid was analyzed by gas chromatography. As a result, 2-Boc-aminopropanol was synthesized at a conversion rate of 51.9% and a selectivity of 89.7%.

Example 5

Hydrogenation of L-Boc-alanine Methyl Ester

L-Boc-alanine methyl ester (2.46 mmol), a ruthenium complex 1 (0.005 mmol), and tetrahydrofuran (1 mL) were charged into a 100-mL autoclave equipped with a stirrer. Then, the mixture was subjected to hydrogenation at a hydrogen pressure of 5 MPa at 120° C. for 8.0 hours. The reaction liquid was analyzed by gas chromatography. As a result, 2-Boc-aminopropanol was synthesized at a conversion rate of 77.7% and a selectivity of 93.4%. The obtained alcohol had an optical purity of 98.2% ee.

Example 6

Hydrogenation of L-Boc-alanine Methyl Ester

L-Boc-alanine methyl ester (5 mmol), a ruthenium complex 1 (0.025 mmol), and tetrahydrofuran (2 mL) were charged into a 100-mL autoclave equipped with a stirrer. Then, the mixture was subjected to hydrogenation at a hydrogen pressure of 5 MPa at 80° C. for 16 hours. The reaction solution was diluted with 20 mL of diethyl ether, and was passed through 10 g of silica gel. The silica gel was washed with diethyl ether. The solution thus obtained was concentrated under reduced pressure. The residue was purified by silica gel column chromatography (silica gel 15 g, hexane/ethyl acetate=2/1 to 1/1). Thus, 2-Boc-aminopropanol (739 mg, 98.4% ee) was obtained.

Example 7

Hydrogenation of L-Boc-alanine Methyl Ester

L-Boc-alanine methyl ester (5 mmol), a ruthenium complex 1 (0.025 mmol), and tetrahydrofuran (2 mL) were charged into a 100-mL autoclave equipped with a stirrer. Then, the mixture was subjected to hydrogenation at a hydrogen pressure of 5 MPa at 100° C. for 16 hours. The reaction solution was diluted with 20 mL of diethyl ether, and was passed through 10 g of silica gel. The silica gel was washed with diethyl ether. The solution thus obtained was concentrated under reduced pressure. The residue was purified by silica gel column chromatography (silica gel 15 g, hexane/ethyl acetate=2/1 to 1/1). Thus, 2-Boc-aminopropanol (719 mg, 98.0% ee) was obtained.

Example 8

Hydrogenation of Methyl (S)-2-methyl-3-phenylpropionate

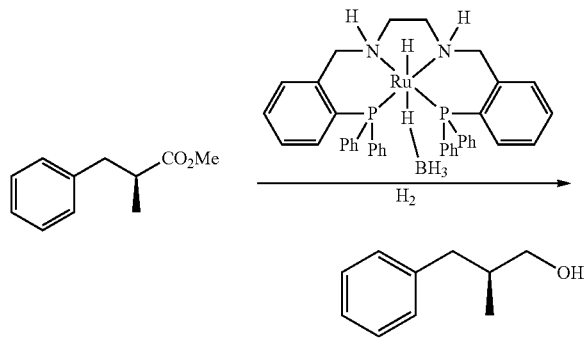

Methyl (S)-2-methyl-3-phenylpropionate (5 mmol, 78.4% ee), a ruthenium complex 1 (0.01 mmol), and tetrahydrofuran (2 mL) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, (S)-2-methyl-3-phenylpropanol was obtained at a conversion rate of 99.0% and a selectivity of 98.6%. The obtained alcohol had an optical purity of 77.9% ee.

Example 9

Hydrogenation of Methyl (R)-3-aminobutanoate

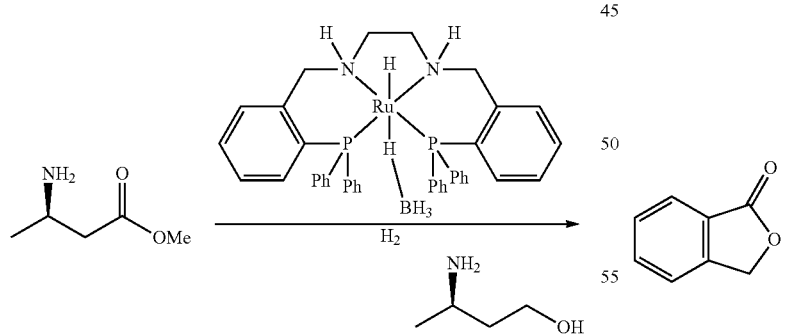

A ruthenium complex 1 (0.333 mmol) was charged into a 100-mL autoclave equipped with a stirrer, and air inside the autoclave was replaced with nitrogen. Tetrahydrofuran (40 mL) and methyl (R)-3-aminobutanoate (100 mmol, 99% ee or more) were charged thereinto. Then, the mixture was subjected to hydrogenation at a hydrogen pressure of 3.5 MPa to 5 MPa at 80° C. for 14 hours. The reaction liquid was concentrated, and the obtained residue was distilled. Thus, (R)-3-aminobutanol (7.39 g; boiling point of 84 to 86° C./14 Torr) was obtained. The obtained alcohol had an optical purity of 99% ee or more.

Example 10

Hydrogenation of Methyl 3-dimethylaminopropionate

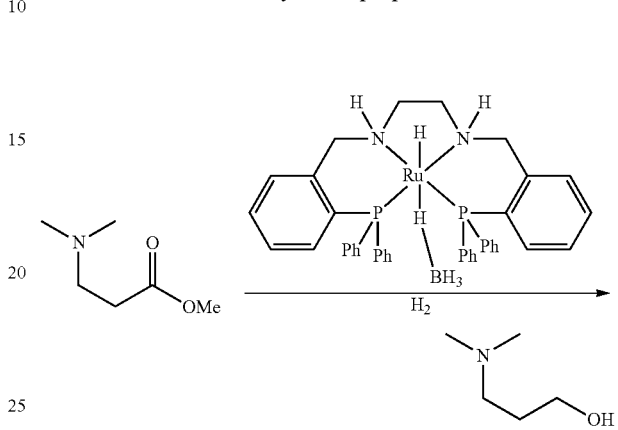

Methyl 3-dimethylaminopropionate (5 mmol), a ruthenium complex 1 (0.05 mmol), and tetrahydrofuran (2 mL) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, 3-dimethylaminopropanol was obtained at a conversion rate of 100% and a selectivity of 97.5%.

Example 11

Hydrogenation of Phthalide

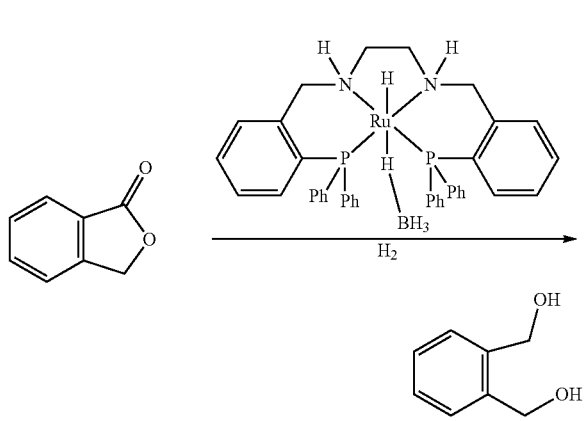

Phthalide (5 mmol), a ruthenium complex 1 (0.025 mmol), and tetrahydrofuran (2 mL) were charged into a 100-mL autoclave equipped with a stirrer. Then, the mixture was subjected to hydrogenation at a hydrogen pressure of 5 MPa at 100° C. for 16 hours. The reaction liquid was analyzed by gas chromatography. As a result, 1,2-benzenedimethanol was obtained at a conversion rate of 66% and a selectivity of 99% or more.

Example 12

Hydrogenation of Methyl Nicotinate

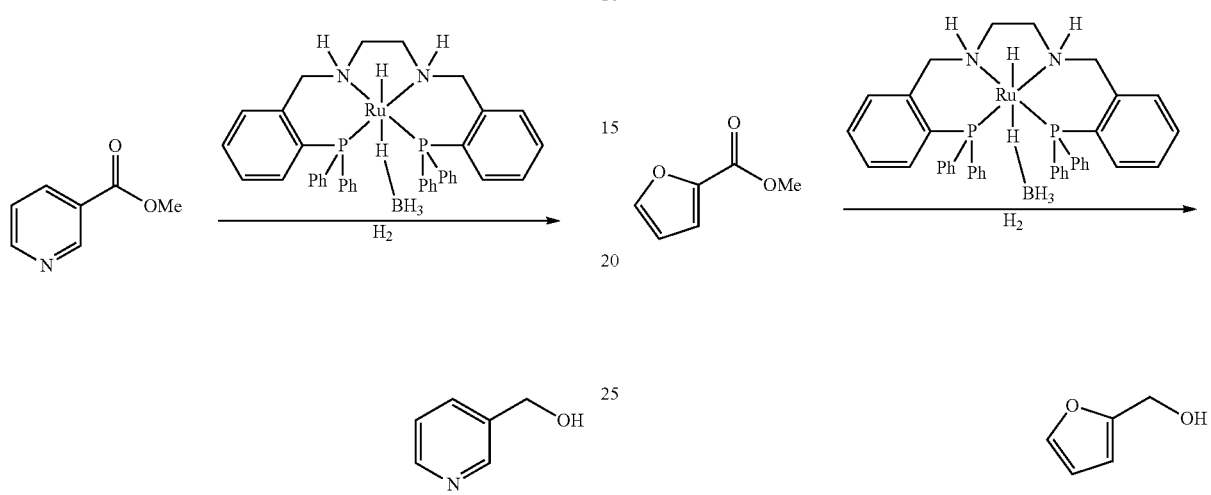

Methyl nicotinate (8 mmol), a ruthenium complex 1 (0.008 mmol), and tetrahydrofuran (3.2 mL) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, 3-pyridinemethanol was obtained at a conversion rate of 42% and a selectivity of 99% or more.

Example 13

Hydrogenation of Benzyl Benzoate

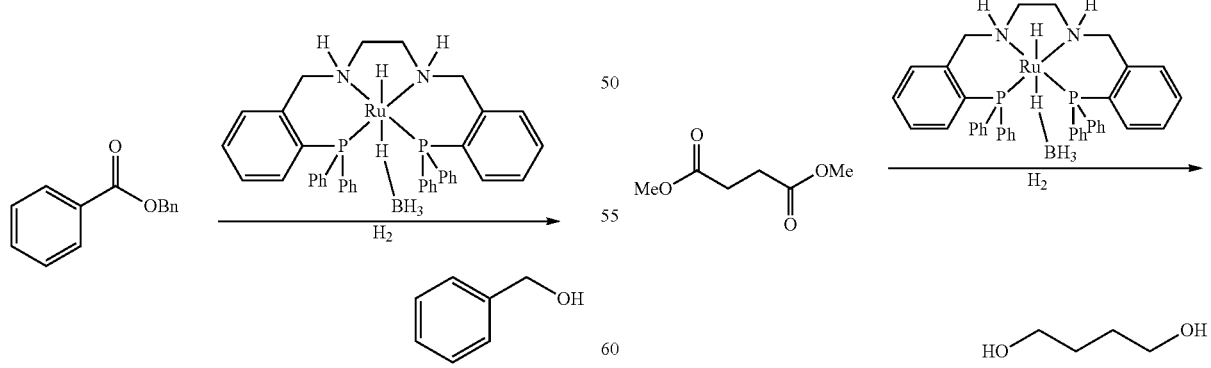

Benzyl benzoate (8 mmol), a ruthenium complex 1 (0.008 mmol), and tetrahydrofuran (3.2 mL) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, benzyl alcohol was obtained at a conversion rate of 23% and a selectivity of 98%.

Example 14

Hydrogenation of Methyl 2-furoate

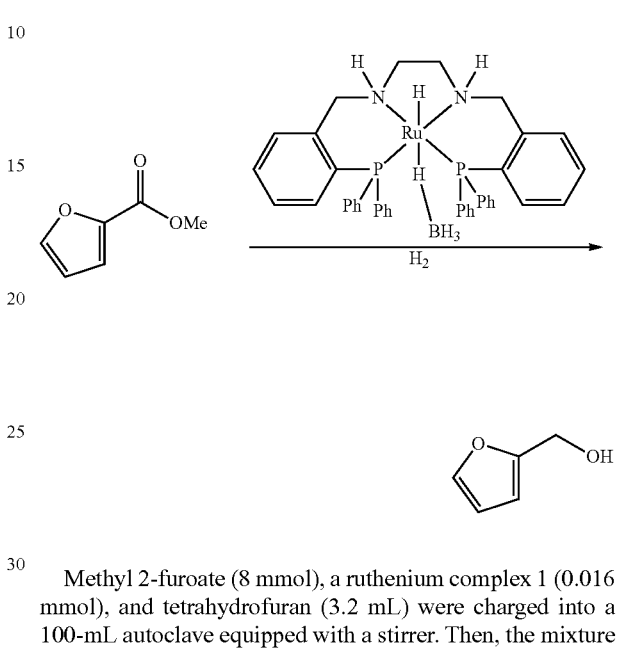

Methyl 2-furoate (8 mmol), a ruthenium complex 1 (0.016 mmol), and tetrahydrofuran (3.2 mL) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, furfuryl alcohol was obtained at a conversion rate of 33% and a selectivity of 99% or more.

Example 15

Hydrogenation of Dimethyl Succinate

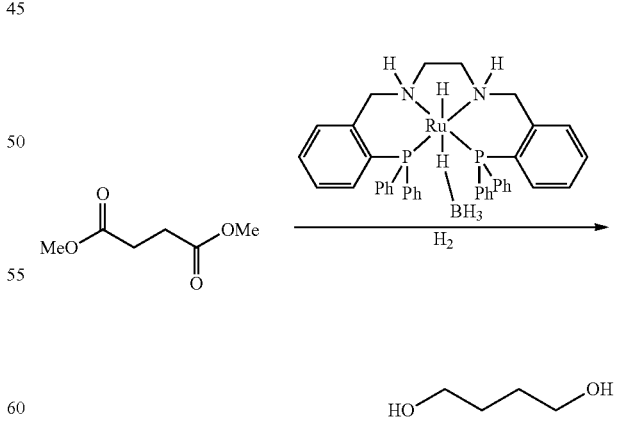

Dimethyl succinate (8 mmol), a ruthenium complex 1 (0.016 mmol), and tetrahydrofuran (3.2 mL) were charged into a 100-mL autoclave equipped with a stirrer. Then, the mixture was subjected to hydrogenation at a hydrogen pressure of 5 MPa at 80° C. for 16 hours. The reaction liquid was

Example 16

Hydrogenation of Methyl (R)-2-hydroxypropionate

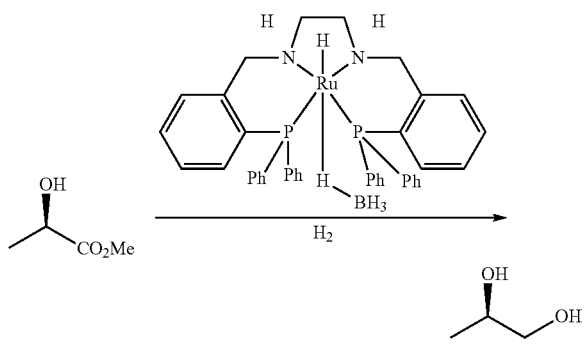

A ruthenium complex 1 (0.125 mmol) was charged into a 100-mL autoclave equipped with a stirrer, and air inside the autoclave was replaced with nitrogen. Tetrahydrofuran (40 ml) and methyl (R)-2-hydroxypropionate (25 mmol, 99.3% ee) were added thereinto. Then, the mixture was subjected to hydrogenation at a hydrogen pressure of 4.6 MPa to 5 MPa at 80° C. for 5 hours. The reaction liquid was analyzed by gas chromatography. As a result, (R)-1,2-propanediol was obtained at a conversion rate of 98.6% and a selectivity of 98.4%. The obtained alcohol had an optical purity of 96.6% ee.

Example 17

Synthesis of Ruthenium Complex 3

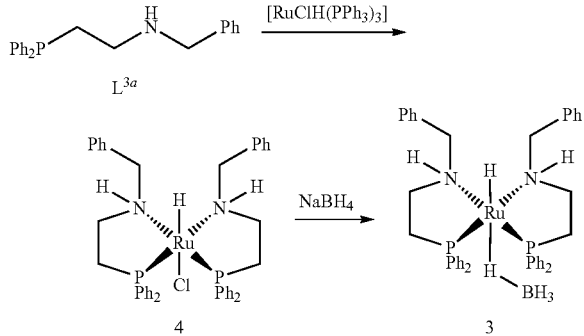

[RuClH(PPh$_3$)$_3$] (1.22 mmol) and L$^{3a}$ (2.44 mmol) were charged into a 100 ml-flask, and air inside the flask was replaced with nitrogen. Then, toluene (15 ml) was added to dissolve [RuClH(PPh$_3$)$_3$] and L$^{3a}$. After 1 hour and 30 minutes of heating at 70° C. and then 30 minutes of cooling in an ice bath, a deposited crystal was filtered under nitrogen atmosphere, and washed with diethyl ether. The resultant crystal was dried under reduced pressure, and a ruthenium complex 4 (790 mg) was obtained. The isomer ratio was 2:1 based on the area ratio of the hydride on the ruthenium according to $^1$H NMR.

The signals of the hydride on the ruthenium were as follows.

$^1$H NMR (300 MHz, CD$_2$Cl$_2$):
Major isomer; δ −19.79 (t, J=28.2 Hz)
Minor isomer; δ −19.58 (dd, J=24.9 Hz, 30.0 Hz)
$^{31}$P NMR (121.5 MHz, CD$_2$Cl$_2$):
Major isomer; δ 75.48 (d, J=24.7 Hz)
Minor isomer; δ 77.1 (d, J=36.2 Hz), 73.2 (d, J=36.2 Hz)

Under a stream of nitrogen, the ruthenium complex 4 (0.7 mmol) was suspended in toluene (15 ml). A solution of sodium borohydride (11.1 mmol) in ethanol (15 ml) was added, and the mixture was heated at 70° C. for 15 minutes, and then stirred at room temperature for 1 hour, air-cooled, and concentrated under reduced pressure. After that, toluene (30 ml) was added, and the mixture was stirred for 20 minutes and celite-filtered. The celite was washed with toluene (10 ml). Under reduced pressure, most of the toluene was collected, and hexane (10 ml) was added. A deposited crystal was filtered. The crystal was washed with diethyl ether, and thus a ruthenium complex 3 (390 mg) was obtained.

$^1$H NMR (300 MHz, CD$_2$Cl$_2$):
δ=−15.70 (t, J=26.7 Hz, 1H), −1.8 (br, 4H), 2.25 (m, 2H), 2.39 (m, 2H), 2.65 (m, 2H), 2.92 (m, 2H), 3.86 (t, J=12.3 Hz, 2H), 4.16-4.52 (m, 4H), 6.87-7.50 (m, 30H)
$^{31}$P NMR (121.5 MHz, CD$_2$Cl$_2$):
δ=77.4

Example 18

Synthesis of Ruthenium Complex 3

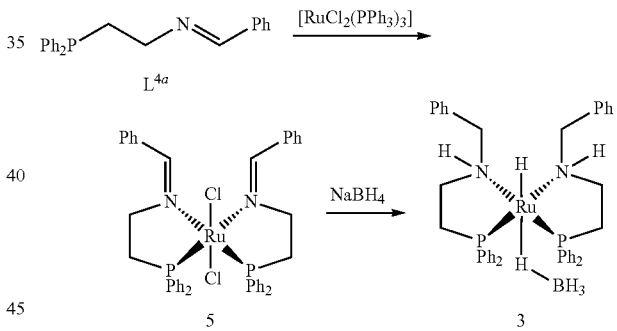

[RuCl$_2$(PPh$_3$)$_3$] (0.75 mmol) and L$^{4a}$ (1.58 mmol) were charged into a 100 ml-flask, and air inside the flask was replaced with nitrogen. Then, toluene (5 ml) was added to dissolve [RuCl$_2$(PPh$_3$)$_3$] and L$^{4a}$. After 40 minutes of heating at 80° C. and then cooling to room temperature, a deposited crystal was filtered under nitrogen atmosphere, and washed with toluene and diethyl ether. The resultant crystal was dried under reduced pressure, and a ruthenium complex 5 (450 mg) was obtained.

$^1$H NMR (300 MHz, C$_6$D$_6$):
δ=2.50 (m, 4H), 4.72 (m, 4H), 6.90-7.10 (m, 22H), 7.48-7.54 (m, 8H), 9.22 (S, 2H)
$^{31}$P NMR (121.5 MHz, C$_6$D$_6$):
δ=55.9

Under a stream of nitrogen, the ruthenium complex 5 (0.12 mmol) was dissolved in toluene (4 ml). A solution of sodium borohydride (1.3 mmol) in ethanol (4 ml) was added, and the mixture was heated at 80° C. for 1 hour. Then, sodium borohydride (1.3 mmol) was added, and the mixture was heated at 80° C. for 1 hour. Sodium borohydride (1.3 mmol) was further added, and stirred at 80° C. for 10 minutes and subsequently at room temperature for 30 minutes, then air-cooled, and concentrated under reduced pressure. After that, toluene (10 ml) was added, and the mixture was stirred for 30 minutes and celite-filtered. Under reduced pressure, most of the toluene was collected, and heptane (3 ml) was added. A deposited crystal was filtered under nitrogen atmosphere. The crystal was washed with heptane, and thus a ruthenium complex 3 (20 mg) was obtained.

$^1$H NMR (300 MHz, CD$_2$Cl$_2$):
δ=−15.70 (t, J=26.7 Hz, 1H), −1.8 (br, 4H), 2.25 (m, 2H), 2.39 (m, 2H), 2.65 (m, 2H), 2.92 (m, 2H), 3.86 (t, J=12.3 Hz, 2H), 4.16-4.52 (m, 4H), 6.87-7.50 (m, 30H)

$^{31}$P NMR (121.5 MHz, CD$_2$Cl$_2$):
δ=77.4

Example 19

Hydrogenation of Methyl Benzoate

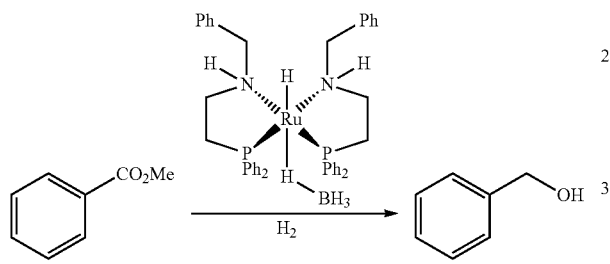

Methyl benzoate (8 mmol), a ruthenium complex 3 (0.008 mmol), and tetrahydrofuran (4 ml) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, benzyl alcohol was obtained at a conversion rate of 100% and a selectivity of 99.1%.

Example 20

Hydrogenation of L-Boc-alanine Methyl Ester

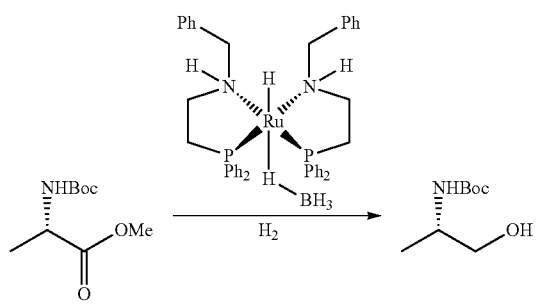

L-Boc-alanine methyl ester (5 mmol), a ruthenium complex 3 (0.01 mmol), and tetrahydrofuran (2 ml) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, 2-Boc-amino-propanol was synthesized at a conversion rate of 77.9% and a selectivity of 80.3%. The obtained alcohol had an optical purity of 99.3% ee.

Example 21

Hydrogenation of Methyl (R)-3-hydroxybutanoate

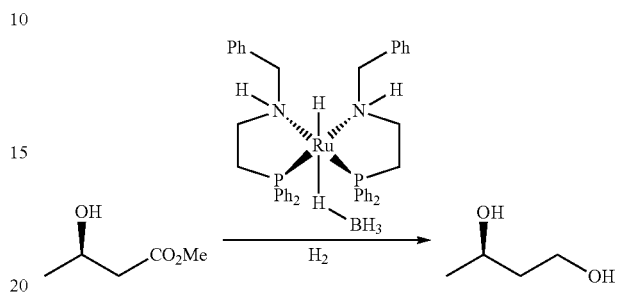

Methyl (R)-3-hydroxybutanoate (5 mmol, 98.9% ee), a ruthenium complex 3 (0.05 mmol), and tetrahydrofuran (2 ml) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, (R)-1,3-butanediol was obtained at a conversion rate of 57.8% and a selectivity of 95.0%. The obtained alcohol had an optical purity of 98.9% ee.

Example 22

Synthesis of Ruthenium Complex 6

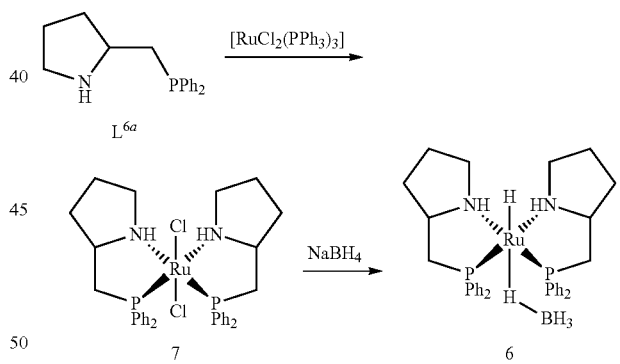

[RuCl$_2$(PPh$_3$)$_3$] (0.93 mmol) and L$^{6a}$ (1.86 mmol) were charged into a 100 ml-flask, and air inside the flask was replaced with nitrogen. Then, toluene (10 ml) was added to dissolve [RuCl$_2$(PPh$_3$)$_3$] and L$^{6a}$. After 1 hour and 30 minutes of heating at 100° C., most of toluene was collected under reduced pressure, and hexane (6 ml) was added. A deposited crystal was filtered under nitrogen atmosphere. The resultant crystal was dried under reduced pressure, and a ruthenium complex 7 (578 mg) was obtained.

$^{31}$P NMR (121.5 MHz C$_6$D$_6$):
δ 53.5

Under a stream of nitrogen, the ruthenium complex 7 (0.81 mmol) was dissolved in toluene (9 ml). A solution of sodium borohydride (12.2 mmol) in ethanol (9 ml) was added, and the mixture was heated at 70° C. for 30 minutes, then stirred at room temperature for 30 minutes, air-cooled, and concentrated under reduced pressure. After that, toluene (18 ml) was added, and the mixture was stirred for 20 minutes and celite-filtered. The celite was washed with toluene (2 ml). Under reduced pressure, most of the toluene was collected, and hexane (4 ml) was added. A deposited crystal was filtered under nitrogen atmosphere. The crystal was washed with diethyl ether, and thus a ruthenium complex 6 (348 mg) was obtained.

$^1$H NMR (300 MHz, C$_6$D$_6$):
δ=−15.26 (dd, J=23.4 Hz, J=26.7 Hz, 1H), −1.1 (br, 4H), 1.02-1.11 (m, 1H), 1.28-1.63 (m, 7H), 2.12-2.55 (m, 6H), 2.98-3.14 (m, 3H), 3.43-3.51 (m, 1H), 4.41 (br, 1H), 4.88-4.99 (m, 1H), 6.88-7.17 (m, 12H), 7.32-7.39 (m, 2H), 7.46-7.52 (m, 2H), 7.60-7.70 (m, 4H)

$^{31}$P NMR (121.5 MHz, C$_6$D$_6$):
δ=74.5 (d, J=34.5 Hz), 79.7 (d, J=34.5 Hz)

Example 23

Hydrogenation of L-Boc-alanine Methyl Ester

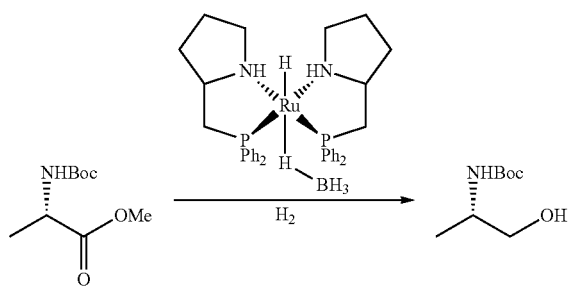

L-Boc-alanine methyl ester (5 mmol), a ruthenium complex 6 (0.05 mmol), and tetrahydrofuran (2 ml) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, 2-Boc-aminopropanol was synthesized at a conversion rate of 99.8% and a selectivity of 98.3%. The obtained alcohol had an optical purity of 98.6% ee.

Comparative Example 1

Hydrogenation of L-Boc-Alanine Methyl Ester Under Condition that Dichlororuthenium Complex 8 was used without Adding Base

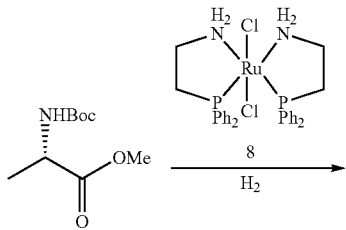

L-Boc-alanine methyl ester (5.0 mmol), a dichlororuthenium complex 8 (0.05 mmol), and tetrahydrofuran (2 ml) were charged into a 100-mL autoclave equipped with a stirrer. Then, the mixture was subjected to hydrogenation at a hydrogen pressure of 5 MPa at 80° C. for 18.0 hours. The reaction liquid was analyzed by gas chromatography. As a result, no alcohol was observed, and the raw material, i.e., the ester, remained.

Comparative Example 2

Hydrogenation of L-Boc-Alanine Methyl Ester Under Condition that Dichlororuthenium Complex 8 was Used with Adding Base

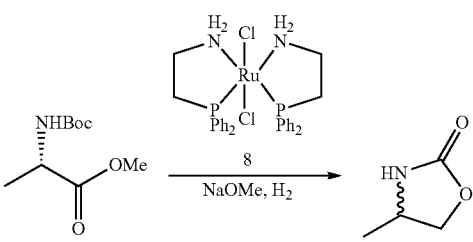

L-Boc-alanine methyl ester (5.0 mmol), sodium methoxide (5 mmol), a dichlororuthenium complex 8 (0.05 mmol), and tetrahydrofuran (2 mL) were charged into a 100-mL autoclave equipped with a stirrer. Then, the mixture was subjected to hydrogenation at a hydrogen pressure of 5 MPa at 80° C. for 18.0 hours. The reaction solution was diluted with 5 mL of methanol and 20 mL of diethyl ether, and purified with 10.0 g of silica gel (diethyl ether/methanol=10/1). A racemic body of 4-methyl-2-oxazolidinone (356 mg) was obtained.

Comparative Example 3

Hydrogenation of Methyl (S)-2-Methyl-3-Phenylpropionate Under Condition that Dichlororuthenium Complex 8 was Used without Adding Base

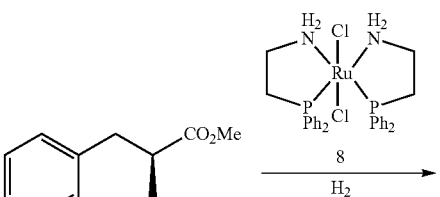

Methyl (S)-2-methyl-3-phenylpropionate (5 mmol, 78.4% ee), a dichlororuthenium complex 8 (0.05 mmol), and tetrahydrofuran (2 mL) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, no alcohol was observed, and the raw material, i.e., the ester, remained.

Comparative Example 4

Hydrogenation of Methyl (S)-2-methyl-3-Phenylpropionate Under Condition that Dichlororuthenium Complex 8 was Used with Adding Base

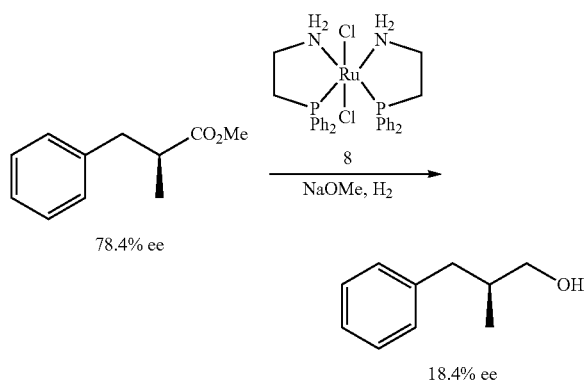

Methyl (S)-2-methyl-3-phenylpropionate (5 mmol, 78.4% ee), a dichlororuthenium complex 8 (0.05 mmol), sodium methoxide (5 mmol), and tetrahydrofuran (2 mL) were charged into a 100-mL autoclave equipped with a stirrer. Then, the mixture was subjected to hydrogenation at a hydrogen pressure of 5 MPa at 80° C. for 16 hours. The reaction solution was diluted with 20 mL of diethyl ether, and was passed through 8.9 g of silica gel. The silica gel was washed with diethyl ether. The solution thus obtained was concentrated under reduced pressure. The residue was purified by silica gel column chromatography (silica gel 13.4 g, hexane/ethyl acetate=8/1). Thus, (S)-2-methyl-3-phenylpropanol (645 mg, 18.4% ee) was obtained.

Comparative Example 5

Hydrogenation of L-Boc-Alanine Methyl Ester with Adding Base

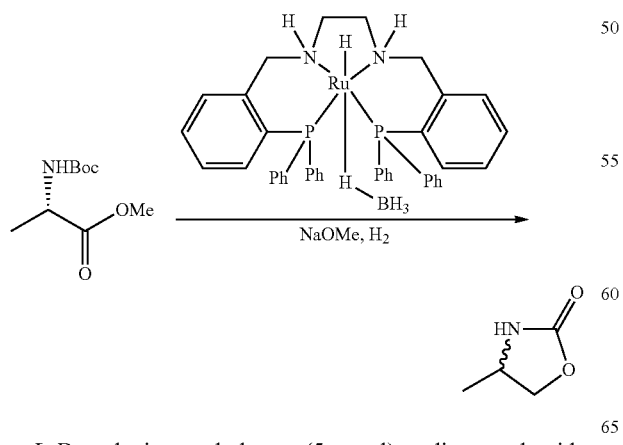

L-Boc-alanine methyl ester (5 mmol), sodium methoxide (5 mmol), a ruthenium complex 1 (0.025 mmol), and tetrahydrofuran (2 mL) were charged into a 100-mL autoclave equipped with a stirrer. Then, the mixture was subjected to hydrogenation at a hydrogen pressure of 5 MPa at 100° C. for 16 hours. The reaction solution was diluted with 5 mL of methanol and 20 mL of diethyl ether, and was passed through 10.0 g of silica gel. The silica gel was washed with diethyl ether. The solution thus obtained was concentrated under reduced pressure. The residue was purified by silica gel column chromatography (silica gel 15.0 g, hexane/ethyl acetate=1/2). A racemic body of 4-methyl-2-oxazolidinone (322 mg) was obtained.

Comparative Example 6

Hydrogenation of Methyl (S)-2-methyl-3-Phenylpropionate with Adding Base

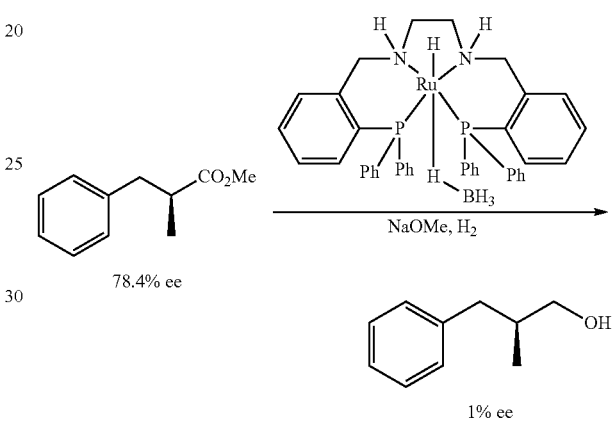

Methyl (S)-2-methyl-3-phenylpropionate (5 mmol, 78.4% ee), sodium methoxide (1 mmol), a ruthenium complex 1 (0.01 mmol), and tetrahydrofuran (2 mL) were charged into a 100-mL autoclave equipped with a stirrer. Then, the mixture was subjected to hydrogenation at a hydrogen pressure of 5 MPa at 80° C. for 16 hours. The reaction solution was diluted with 20 mL of diethyl ether, and was passed through 8.9 g of silica gel. The silica gel was washed with diethyl ether. The obtained solution was concentrated under reduced pressure. The residue was purified by silica gel column chromatography (silica gel 13.4 g, hexane/ethyl acetate=8/1). (S)-2-Methyl-3-phenylpropanol (657 mg, 1% ee) was obtained.

Comparative Example 7

Hydrogenation of Methyl (R)-3-Aminobutanoate with Adding Base

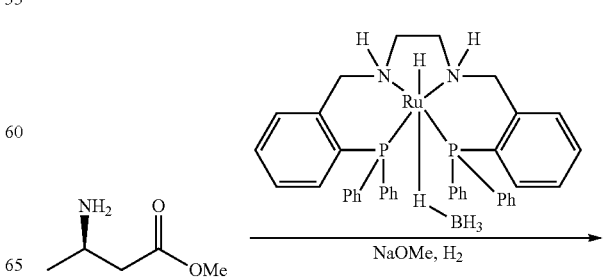

Methyl (R)-3-aminobutanoate (5 mmol), sodium methoxide (1 mmol), a ruthenium complex 1 (0.05 mmol), and tetrahydrofuran (2 mL) were charged into a 100-mL autoclave equipped with a stirrer. Then, the mixture was subjected to hydrogenation at a hydrogen pressure of 5 MPa at 80° C. for 16 hours. The reaction liquid was analyzed by gas chromatography. As a result, the reaction gave a complicated mixture, and the raw material disappeared; however, a targeted alcohol was not synthesized.

What is claimed is:

1. A method for producing an alcohol, the method comprising the step of reducing an ester or a lactone with hydrogen to produce a corresponding alcohol without addition of a base compound in the presence of, as a catalyst, a ruthenium complex represented by the following general formula (1):

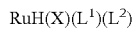
(1)

wherein

X represents $BH_4$, $L^1$ and $L^2$ each represent a bidentate ligand represented by the following general formula (3):

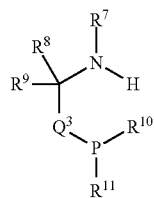
(3)

wherein $R^7$, $R^8$, $R^9$, $R^{10}$ and $R^{11}$, which may be same or different, each represent a hydrogen atom, an alkyl group which may have a substituent, an aryl group which may have a substituent, an aralkyl group which may have a substituent, or a cycloalkyl group which may have a substituent, $R^7$ and $R^8$, $R^7$ and $R^9$, $R^8$ and $R^9$, or $R^{10}$ and $R^{11}$ may bond to each other to form a ring, and $Q^3$ represents a divalent arylene group which may have a substituent, an alkylene group which may have a substituent, or a bond.

2. The production method according to claim 1, wherein the complex is obtained by reducing a ruthenium complex including a bidentate ligand represented by the following general formulae (7a) or (7b):

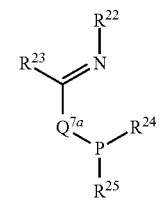
(7a)

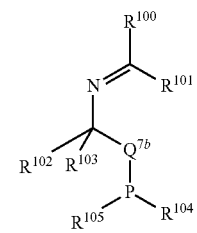
(7b)

wherein $R^{22}$, $R^{23}$, $R^{24}$, $R^{25}$, $R^{100}$, $R^{101}$, $R^{102}$, $R^{103}$, $R^{104}$ and $R^{105}$, which may be same or different, each represent a hydrogen atom, an alkyl group which may have a substituent, an aryl group which may have a substituent, an aralkyl group which may have a substituent, or a cycloalkyl group which may have a substituent, $R^{22}$ and $R^{23}$, $R^{24}$ and $R^{25}$, or $R^{104}$ and $R^{105}$ may bond to each other to form a ring, and $Q^{7a}$ and $Q^{7b}$ each represent a divalent arylene group which may have a substituent, an alkylene group which may have a substituent, or a bond, the ruthenium complex being represented by a general formula (6'):

$$[Ru(X^3)(X^4)(L^{1''})(L^{2''})]$$ (6')

wherein $X^3$ and $X^4$ each independently represent a hydrogen atom or halogen atom, and $L^{1''}$ and $L^{2''}$, which may be same or different, each represent the bidentate ligand represented by the general formula (7a) or (7b).

3. The production method according to claim 1, wherein the prepared complex is used as the catalyst without being isolated from a complex preparing solution.

4. The production method according to claim 1, wherein the ester or the lactone is an optically active substance, and the obtained alcohol holds an optical purity of 90% or more of that of the ester or lactone reduced with hydrogen.

5. The production method according to claim 2, wherein the prepared complex is used as the catalyst without being isolated from a complex preparing solution.

* * * * *